(12) United States Patent
Sano et al.

(10) Patent No.: US 11,083,396 B2
(45) Date of Patent: Aug. 10, 2021

(54) PORTABLE ELECTRONIC APPARATUS

(71) Applicant: SEIKO EPSON CORPORATION, Tokyo (JP)

(72) Inventors: Fumikazu Sano, Matsumoto (JP); Kazuhiro Shibuya, Shiojiri (JP)

(73) Assignee: SEIKO EPSON CORPORATION, Tokyo (JP)

( * ) Notice: Subject to any disclaimer, the term of this patent is extended or adjusted under 35 U.S.C. 154(b) by 299 days.

(21) Appl. No.: 16/030,282

(22) Filed: Jul. 9, 2018

(65) Prior Publication Data

US 2019/0015017 A1   Jan. 17, 2019

(30) Foreign Application Priority Data

Jul. 14, 2017  (JP) .............................. JP2017-137777

(51) Int. Cl.
  *A61B 5/00* (2006.01)
  *A61B 5/11* (2006.01)
  *A63B 71/06* (2006.01)
  *G16H 20/30* (2018.01)

(52) U.S. Cl.
  CPC ............ *A61B 5/1123* (2013.01); *A61B 5/681* (2013.01); *A61B 5/742* (2013.01); *A63B 71/0686* (2013.01); *G16H 20/30* (2018.01); *A61B 5/7285* (2013.01); *A63B 2071/065* (2013.01); *A63B 2220/17* (2013.01); *A63B 2220/62* (2013.01); *A63B 2220/64* (2013.01); *A63B 2220/836* (2013.01)

(58) Field of Classification Search
  CPC ................. G06F 3/011; G06F 3/04842; A61B 2562/0219; A61B 5/11; A61B 5/1117; A61B 5/1118; A61B 5/1123; A61B 5/681; A61B 5/742; A61B 5/7285; G16H 20/30; A63B 71/0686; A63B 2220/836; A63B 2071/065; A63B 2220/17; A63B 2220/62; A63B 2220/64
  USPC .......... 600/300, 310, 587, 595; 473/212, 221
  See application file for complete search history.

(56) References Cited

U.S. PATENT DOCUMENTS 9,261,526 B2 *  2/2016  Bentley ................ A61B 5/6895
9,607,652 B2 *  3/2017  Bose ....................... G11B 27/34
D801,365 S  * 10/2017  Broughton ................... D14/486
(Continued)

FOREIGN PATENT DOCUMENTS

JP    2010-022740 A     2/2010
JP    2014-230630 A    12/2014
(Continued)

*Primary Examiner* — May A Abouelela
(74) *Attorney, Agent, or Firm* — Oliff PLC

(57) ABSTRACT

A portable electronic apparatus includes an operation section adapted to receive an operation of a user and output a rest start signal representing start of a rest, a body motion sensor adapted to output a body motion signal based on a motion of the user, a timing section adapted to measure rest time of the user, and a processor electrically connected to the operation section, the body motion sensor, and the timing section, and the processor starts the measurement of the rest time by the timing section in the case in which the processor fails to detect the rest start signal, and fails to detect the periodic component based on the motion of the user in the body motion signal for a predetermined period.

17 Claims, 20 Drawing Sheets

(56) References Cited

U.S. PATENT DOCUMENTS

| | | | | |
|---|---|---|---|---|
| 2004/0133081 A1* | 7/2004 | Teller | A61B 5/743 | 600/300 |
| 2012/0316455 A1* | 12/2012 | Rahman | G01C 22/006 | 600/547 |
| 2013/0012836 A1* | 1/2013 | Crespo Veiga | A61B 5/7221 | 600/595 |
| 2013/0018284 A1* | 1/2013 | Kahn | A61B 5/681 | 600/595 |
| 2013/0184613 A1* | 7/2013 | Homsi | G06F 17/00 | 600/595 |
| 2014/0073994 A1* | 3/2014 | Machado | A61B 5/0015 | 600/595 |
| 2014/0378239 A1* | 12/2014 | Sato | G06K 9/00355 | 473/199 |
| 2014/0379295 A1* | 12/2014 | Sato | G01P 15/02 | 702/142 |
| 2015/0173655 A1* | 6/2015 | Demmer | A61B 5/686 | 600/595 |
| 2015/0223705 A1* | 8/2015 | Sadhu | G08B 21/0446 | 600/301 |
| 2016/0051168 A1* | 2/2016 | Kamali | A61B 5/1123 | 600/595 |
| 2016/0058337 A1* | 3/2016 | Blahnik | A61B 5/1112 | 600/595 |
| 2016/0058372 A1* | 3/2016 | Raghuram | A61B 5/1112 | 600/595 |
| 2016/0058378 A1* | 3/2016 | Wisbey | A61B 5/1118 | 600/479 |
| 2016/0066844 A1* | 3/2016 | Venkatraman | A61B 5/02416 | 702/141 |
| 2016/0081630 A1* | 3/2016 | Aoshima | A61B 5/0205 | 600/301 |
| 2016/0192874 A1* | 7/2016 | Canavan | A61B 5/1114 | 600/595 |
| 2017/0164851 A1* | 6/2017 | Takahashi | A61B 5/2438 | |
| 2017/0319941 A1* | 11/2017 | Smith | A63B 21/153 | |
| 2018/0001174 A1 | 1/2018 | Aoshima et al. | | |
| 2018/0036531 A1* | 2/2018 | Schwarz | A61N 1/0484 | |
| 2019/0083034 A1* | 3/2019 | Shim | A61B 5/14551 | |

FOREIGN PATENT DOCUMENTS

| | | |
|---|---|---|
| JP | 2018-000543 A | 1/2018 |
| WO | 2004/015606 A1 | 2/2004 |

* cited by examiner

PORTABLE ELECTRONIC APPARATUS

CROSS-REFERENCES TO RELATED APPLICATIONS

This application claims priority to Japanese Patent Application No. 2017-137777, filed Jul. 14, 2017, the entirety of which is herein incorporated by reference.

BACKGROUND

1. Technical Field

The present invention relates to a portable electronic apparatus.

2. Related Art

In recent years, there has been proposed a method of monitoring an amount of exercise and a performance in swimming with a wearable sensing device carried. Specifically, swimming is performed in the state in which a variety of types of sensors are mounted on the body of the swimmer, and sensor signals on this occasion are obtained. A form analysis related to the swimming, measurement of the swimming time, the swimming distance, and the swimming speed, and measurement of the calorie consumption are performed based on the sensor signals thus obtained. Further, the information can also be used for setting goals, planning the workout, executing the workout, composing the racing pace, and reflecting the race.

A measurement device for measuring the performance in the swimming is disclosed in JP-A-2010-22740 (Document 1). According to the disclosure, the measurement device is a portable electronic device installed in the wrist of the user. Further, the measurement device makes the determination on which one of the swimming state, the state of a turning action, and the state of the termination of the swimming the user's state is. The user denotes the user of the measurement device. Then, the measurement device calculates to display the swimming distance and the swimming time of the user, and the calorie consumption.

When performing the workout for swimming, the user repeats the swimming state and the rest state. In the swimming state, the fatigue is accumulated, and in the rest state, the fatigue decreases. The user works out while managing the time spent in the swimming state and the time spent in the rest state. Therefore, in order to accurately manage the workout, it is necessary to accurately detect the time when the swimming state starts, the time when the transition from the swimming state to the rest state is made, the time when the transition from the rest state to the swimming state is made, and a change in state of the user.

The measurement device of Document 1 analyzes whether the user is in the swimming state or the user is in the rest state using the output of an acceleration sensor. On this occasion, in the case in which a periodic component is included in the waveform output by the acceleration sensor, the measurement device determines that the user is in the swimming state. Therefore, it becomes possible to determine that the swimming has been started when the user has repeated a motion a plurality of times. However, in the case of determining that the swimming has been terminated, the determination cannot be made unless a waveform has been analyzed for a predetermined period of time. As described above, in the case of using the acceleration sensor and so on, it is difficult to instantly determine the timing for performing the switching between the swimming state and the rest state.

Therefore, it is conceivable that the user operates a switch or the like at the start and the termination of the swimming to instruct and thus be detected the start and the termination of the swimming. Due to the operations, it is possible to accurately detect the moment when the switching between the swimming state and the rest state has been performed. However, since the fatigue is accumulated when the user continues the swimming state, the attentional capacity decreases. Therefore, the user forgets to make the rest instruction operation in some cases. Therefore, there has been demanded a portable electronic apparatus capable of starting the measurement of the rest time even in the case in which the user forgets to make the rest instruction operation.

SUMMARY

An advantage of some aspects of the invention is to solve the problems described above, and the invention can be implemented as the embodiments or the application examples described below.

APPLICATION EXAMPLE 1

A portable electronic apparatus according to this application example includes an operation section adapted to receive an operation of a user and output a rest start signal representing start of a rest, a body motion sensor adapted to output a body motion signal based on a motion of the user, a timing section adapted to measure rest time of the user, and a processor electrically connected to the operation section, the body motion sensor, and the timing section, and the processor starts measurement of the rest time by the timing section in a case in which the processor fails to detect the rest start signal, and fails to detect a periodic component based on the motion of the user in the body motion signal.

According to this application example, the portable electronic apparatus is provided with the operation section, the body motion sensor, the timing section, and the processor. The operation section receives the operation of the user instructing the start of the rest, and then outputs the rest start signal. The body motion sensor outputs the body motion signal based on the motion of the user. The timing section measures the rest time for which the user takes a rest. Further, the processor is electrically connected to the operation section, the body motion sensor, and the timing section.

In the case in which the user makes the operation of instructing to start the rest, the operation section outputs the rest start signal to the processor. Then, the processor makes the timing section start the measurement of the rest time. In the case in which the user makes the repetitive motion (e.g., swimming or walking), the processor detects the periodic component based on the motion of the user in the body motion signal. In the case in which the user stops the repetitive motion, the periodic component based on the motion of the user is not detected by the processor in the body motion signal. Then, in the case in which the user takes a rest, the repetitive motion is not performed for a predetermined period. When the processor fails to detect the periodic component based on the motion of the user in the body motion signal for the predetermined period, the processor makes the timing section start the measurement of the rest time. Then, the timing section starts the measurement of the rest time. Therefore, even in the case in which the user forgets to operate the operation section when taking a rest, it is possible for the portable electronic apparatus to start the measurement of the rest time.

APPLICATION EXAMPLE 2

In the portable electronic apparatus according to the application example described above, the operation section receives an operation of the user to output an exercise start signal representing start of exercise, and the processor starts measurement of the rest time by the timing section in one of a case in which the processor detects the rest start signal after detecting the exercise start signal, and a case in which the processor fails to detect the rest start signal and fails to detect the periodic component based on the motion of the user in the body motion signal for a predetermined period.

According to this application example, in the case in which the user makes the operation of instructing the start of the exercise, the operation section receives the operation of instructing the start of the exercise and then outputs the exercise start signal to the processor. Subsequently, in the case in which the user makes the operation of instructing the start of the rest, the operation section receives the operation of instructing the start of the rest and then outputs the rest start signal to the processor. On this occasion, the processor detects the exercise start signal, and then detects the rest start signal. Then, the processor makes the timing section start the measurement of the rest time, and therefore, the measurement of the rest time by the timing section is started. Therefore, it is possible to surely start the measurement of the rest time by the timing section based on the instruction of the user.

In the case in which the user makes the operation of instructing the start of the exercise, the operation section receives the operation of instructing the start of the exercise and then outputs the exercise start signal to the processor. Subsequently, in the case in which the user does not make the repetitive motion, the periodic component based on the motion of the user is not detected by the processor in the body motion signal. When the processor fails to detect the periodic component based on the motion of the user in the body motion signal for the predetermined period, the processor makes the timing section start the measurement of the rest time. Then, the timing section starts the measurement of the rest time. Therefore, even in the case in which the user makes the operation of instructing to start the exercise, but forgets to make the operation of instructing to start the rest, it is possible for the portable electronic apparatus to start the measurement of the rest time.

APPLICATION EXAMPLE 3

In the portable electronic apparatus according to the application example described above, the timing section measures exercise time for which the user does the exercise, and the timing section continues the measurement of the exercise time in a case in which the processor detects the periodic component within a predetermined period after turning to a state of not detecting the periodic component while the timing section is measuring the exercise time.

According to this application example, the timing section measures the exercise time for which the user does the exercise in addition to the rest time. Then, in the case in which the user makes the repetitive motion, the timing section measures the exercise time for which the user does the exercise. In the case in which the user stops the repetitive motion, the processor turns to the state of not detecting the periodic component. In the case in which the user resumes the repetitive motion within a predetermined period, the processor detects the periodic component within the predetermined period after the processor has turned to the state of not detecting the periodic component. On this occasion, the processor makes the timing section continue the measurement of the exercise time. Therefore, in the case in which the user resumes the repetitive motion after once stopping the repetitive motion within the predetermined period, the timing section continuously measures the exercise time. As a result, it is possible for the user to make the portable electronic apparatus continue the measurement of the exercise time.

APPLICATION EXAMPLE 4

In the portable electronic apparatus according to the application example described above, there is further included a display section adapted to display rest information related to the rest time measured by the timing section.

According to this application example, the portable electronic apparatus is provided with the display section. The display panel displays the information from the timing section. Then, when the timing section measures the rest time, the display panel displays the rest information related to the rest time. Therefore, it is possible for the user to look at the display section to check the information such as the time having elapsed from the start of the rest.

APPLICATION EXAMPLE 5

In the portable electronic apparatus according to the application example described above, the processor terminates the measurement of the rest time by the timing section in a case in which the processor detects the periodic component based on the motion of the user in the body motion signal for a predetermined period after starting the measurement of the rest time.

According to this application example, after starting the measurement of the rest time, the measurement of the rest time continues. On this occasion, when the periodic component based on the motion of the user is detected in the body motion signal for the predetermined period, the measurement of the rest time by the timing section is terminated. Therefore, even in the case in which the user forgets to operate the operation section, it is possible to terminate the measurement of the rest time.

APPLICATION EXAMPLE 6

A portable electronic apparatus according to this application example includes an operation section adapted to receive an operation of a user and output a rest start signal representing start of a rest, a body motion sensor adapted to output a body motion signal based on a motion of the user, a timing section adapted to measure rest time of the user, a display section adapted to display at least information from the timing section, and a processor electrically connected to the operation section, the body motion sensor, the timing section, and the display section, and the timing section starts the measurement of the rest time and the display section displays rest information related to the rest time in a case in which the processor fails to detect the rest start signal, and fails to detect the body motion signal satisfying a predetermined condition for a predetermined period.

According to this application example, the portable electronic apparatus is provided with the operation section, the body motion sensor, the timing section, the display section, and the processor. The operation section receives the operation of the user instructing the start of the rest, and then outputs the rest start signal. The body motion sensor outputs the body motion signal based on the motion of the user. The timing section measures the rest time for which the user takes a rest. The display panel displays the information from the timing section. Further, the processor is electrically connected to the operation section, the body motion sensor, the timing section, and the display section.

In the case in which the user makes the operation of instructing to start the rest, the operation section outputs the rest start signal to the processor. Then, the processor makes the timing section start the measurement of the rest time. In the case in which the user makes the repetitive motion, the processor detects the periodic component based on the motion of the user in the body motion signal. When the processor detects the body motion signal satisfying a predetermined condition, the fact that the user is doing the repetitive motion is detected. In the case in which the user stops the repetitive motion, the periodic component based on the motion of the user is not detected by the processor in the body motion signal. Then, in the case in which the user takes a rest, the repetitive motion is not performed for a predetermined period. When the processor fails to detect the body motion signal satisfying the predetermined condition based on the motion of the user in the body motion signal for the predetermined period, the processor makes the timing section start the measurement of the rest time. Then, the timing section starts the measurement of the rest time. Therefore, even in the case in which the user forgets to make the rest instruction operation, it is possible for the portable electronic apparatus to start the measurement of the rest time. Further, it is possible for the user to look at the display section to check the information such as the time having elapsed from the start of the rest.

APPLICATION EXAMPLE 7

In the portable electronic apparatus according to the application example described above, the body motion signal satisfying the predetermined condition is a signal including a continuous periodic component.

According to this application example, the body motion signal satisfying the predetermined condition is a signal including the continuous periodic component. Therefore, in the case in which the user continuously performs the repetitive motions, it is possible for the processor to detect the fact that the user is doing exercise.

APPLICATION EXAMPLE 8

A portable electronic apparatus according to this application example includes an operation section adapted to receive an operation of a user and output a rest termination signal representing termination of a rest, a body motion sensor adapted to output a body motion signal based on a motion of the user, a timing section adapted to measure rest time of the user, and a processor electrically connected to the operation section, the body motion sensor, and the timing section, and the timing section terminates measurement of the rest time in a case in which the processor fails to detect the rest termination signal, and fails to detect the body motion signal including a periodic component based on the motion of the user.

According to this application example, the portable electronic apparatus is provided with the operation section, the body motion sensor, the timing section, and the processor. The operation section receives the operation of the user instructing the termination of the rest, and then outputs the rest termination signal. The body motion sensor outputs the body motion signal based on the motion of the user. The timing section measures the rest time for which the user takes a rest. Further, the processor is electrically connected to the operation section, the body motion sensor, and the timing section.

In the case in which the user makes the rest termination instruction operation, the operation section outputs the rest termination signal to the processor. Then, the processor makes the timing section terminate the measurement of the rest time. In the case in which the user forgets to make the rest termination instruction operation, the operation section does not output the rest termination signal to the processor. Then, the processor makes the timing section continue the measurement of the rest time. Even on this occasion, in the case in which the user makes the repetitive motion, the processor detects the periodic component based on the motion of the user in the body motion signal. When the processor detects the periodic component based on the motion of the user in the body motion signal, the processor makes the timing section terminate the measurement of the rest time. Then, the timing section terminates the measurement of the rest time. Therefore, even in the case in which the user forgets to make the operation of instructing the termination of the rest, it is possible for the portable electronic apparatus to terminate the measurement of the rest time.

APPLICATION EXAMPLE 9

In the portable electronic apparatus according to the application example described above, the timing section measures exercise time for which the user does exercise, the operation section receives an operation of the user to output an exercise termination signal representing termination of the exercise, the timing section terminates the measurement of the exercise time in a case in which the processor detects the exercise termination signal while the timing section is measuring the exercise time, and the processor fails to detect the body motion signal including a periodic component based on the motion of the user, and the timing section continues the measurement of the exercise time in a case in which the processor detects the exercise termination signal while the timing section is measuring the exercise time, and the processor detects the body motion signal including the periodic component based on the motion of the user.

According to this application example, the portable electronic apparatus measures the exercise time in addition to the rest time. The operation section receives the operation of the user instructing the termination of the exercise, and then outputs the exercise termination signal. In the case in which the processor detects the exercise termination signal while the timing section is measuring the exercise time, and the processor fails to detect the periodic component, the timing section terminates the measurement of the exercise time. In other words, in the case in which the user stops the repetitive motion and makes the exercise termination instruction operation, the timing section terminates the measurement of the exercise time.

In the case in which the processor detects the exercise termination signal while the timing section is measuring the exercise time, and the processor detects the periodic component, the timing section continues the measurement of the exercise time. In other words, in the case in which the user continues the repetitive motion and makes the exercise termination instruction operation, the timing section continues the measurement of the exercise time. Therefore, in the case in which the operation of instructing the exercise termination is an erroneous operation, it is possible for the timing section to continue the measurement of the exercise time.

APPLICATION EXAMPLE 10

In the portable electronic apparatus according to the application example described above, there is further included a memory adapted to store time at which the operation section outputs the rest termination signal, the operation section receives the operation of the user instructing edit to output an edit signal, and the processor detects the edit signal to terminate the rest time at time at which the rest termination signal is output.

According to this application example, the portable electronic apparatus is provided with the memory, and the memory stores the time at which the operation section outputs the rest termination signal. In the case in which the user makes the edit instruction operation of the rest time, the operation section receives the edit instruction operation of the user. Then, the operation section outputs the edit signal to the processor. The processor detects the edit signal to terminate the rest time at the time at which the rest termination signal is output. Therefore, it is possible to correct the rest time into the correct time in the case in which the rest termination signal is not caused by an erroneous operation.

APPLICATION EXAMPLE 11

In the portable electronic apparatus according to the application example described above, there is further included a display section adapted to display the rest time in a case of measuring the rest time.

According to this application example, the portable electronic apparatus is provided with the display section. The display panel displays the information from the timing section. Then, when the timing section measures the rest time, the display section displays the information representing the rest time. Therefore, it is possible for the user to look at the display section to check the time having elapsed from the start of the rest.

BRIEF DESCRIPTION OF THE DRAWINGS

The invention will be described with reference to the accompanying drawings, wherein like numbers reference like elements.

DESCRIPTION OF AN EXEMPLARY EMBODIMENT

Figure 1:
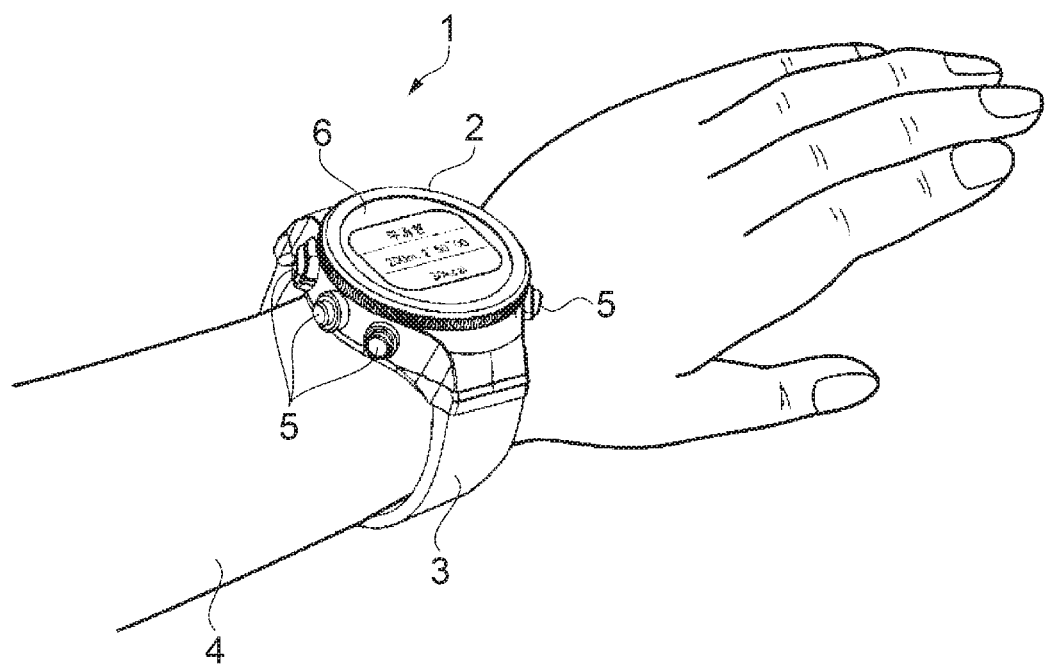
FIG. 1 is a schematic diagram for explaining an installation example of a portable electronic apparatus.

Hereinafter, an embodiment will be described along the accompanying drawings. It should be noted that each of the members in each of the drawings is illustrated with a different scale from each other in order to provide a size large enough to be recognized in the drawing.

Embodiment

In the present embodiment, characteristic examples of a portable electronic apparatus, and a time measurement method for measuring exercise time and rest time using the portable electronic apparatus will be described along the accompanying drawings. The portable electronic apparatus according to the present embodiment will be described along FIG. 1 and FIG. 2. FIG. 1 is a schematic diagram for explaining an installation example of the portable electronic apparatus. As shown in FIG. 1, the portable electronic apparatus 1 is provided with a housing 2 having a roughly disc-like shape, and a wristband 3 is disposed so as to be connected to the housing 2.

By winding the wristband 3 around the wrist of the user 4, the portable electronic apparatus 1 is installed to the user 4. On the side surface of the housing 2, there are installed push buttons 5 as a plurality of operation sections. The user 4 presses the push buttons 5 to input a variety of instructions to the portable electronic apparatus 1. For example, when making an instruction of starting the measurement of the exercise time and an instruction of terminating the measurement thereof, the user 4 presses the push buttons 5. In addition, for example, when making an instruction of starting the measurement of the rest time and an instruction of terminating the measurement thereof, the user 4 presses the push buttons 5.

A display panel 6 as a display section is installed in the housing 2. The display panel 6 displays the present time, the time for which the exercise is performed, and the time for which the rest is taken. As the display panel 6, there can be used a liquid crystal display device, an organic electroluminescence display, a plasma display, or a surface-conduction electron-emitter display.

Figure 2:
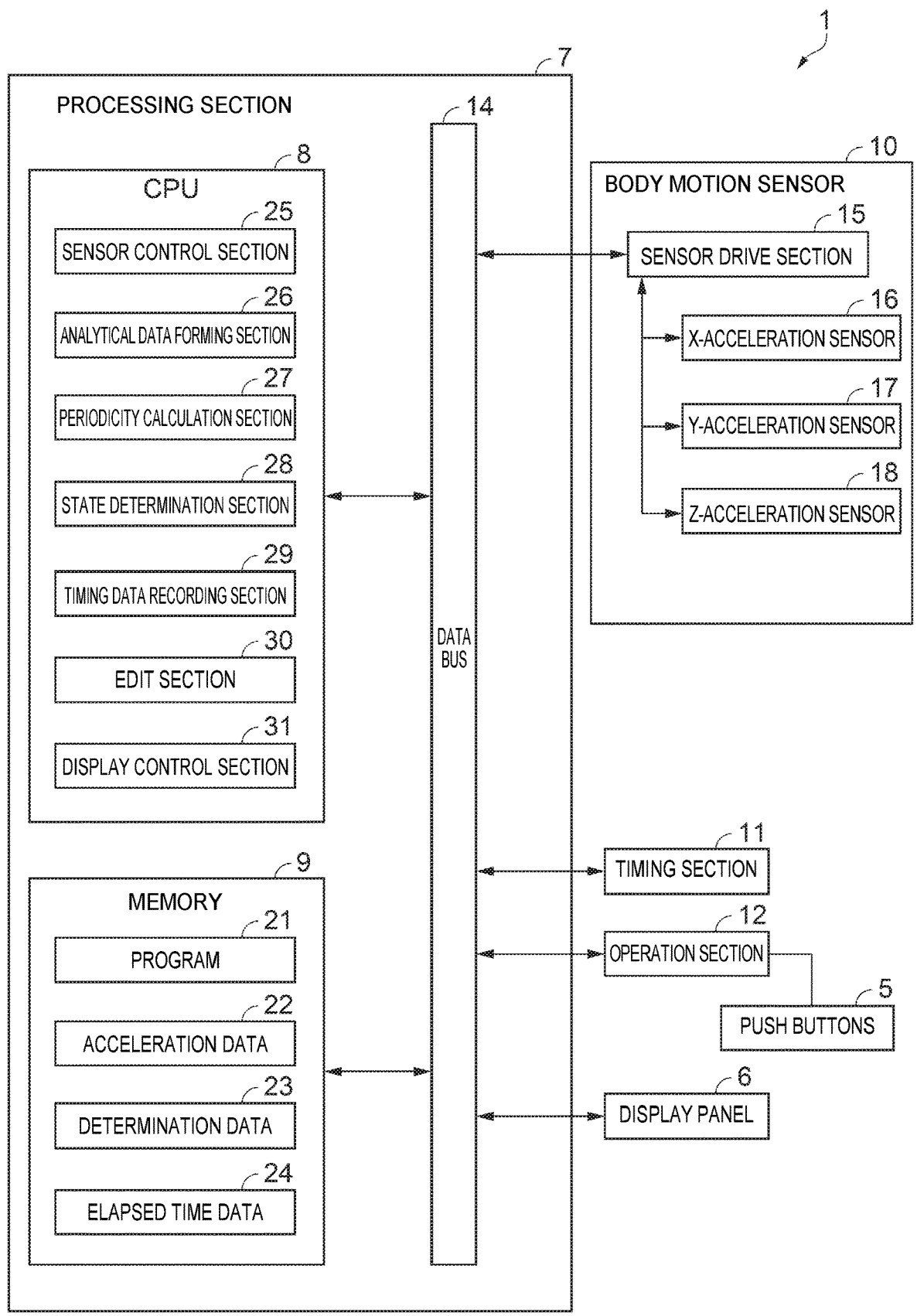
FIG. 2 is a block diagram of electric control of the portable electronic apparatus.

FIG. 2 is a block diagram of electric control of the portable electronic apparatus. In FIG. 2, the portable electronic apparatus 1 is provided with a processing section (processor) 7 for performing the arithmetic processing and the control. Further, the processing section 7 is provided with a central processing unit (CPU) 8 for performing a variety of types of arithmetic processing as a processor, and a memory 9 for storing a variety of types of information. A body motion sensor 10, a timing section 11, an operation section 12, and the display panel 6 are electrically connected to the CPU 8 of the processing section 7 via a data bus 14.

The body motion sensor 10 is provided with a sensor drive section 15, and an X-acceleration sensor 16, a Y-acceleration sensor 17, and a Z-acceleration sensor 18 connected to the sensor drive section 15. The sensor drive section 15 is provided with a drive circuit, and the sensor drive section 15 drives the X-acceleration sensor 16, the Y-acceleration sensor 17, and the Z-acceleration sensor 18. The body motion sensor 10 includes a gyro sensor and a barometric pressure sensor not shown. The gyro sensor detects an angular variation. The barometric pressure sensor detects whether the portable electronic apparatus 1 is in the water or is in the air.

The X-acceleration sensor 16, the Y-acceleration sensor 17 and the Z-acceleration sensor 18 respectively detect acceleration applied in the three directions perpendicular to each other, and then output the result to the sensor drive section 15. These acceleration sensors are each provided with a piezoelectric element, and the piezoelectric element outputs a voltage signal corresponding to the acceleration to the sensor drive section 15.

The sensor drive section 15 inputs the voltage signals from the X-acceleration sensor 16, the Y-acceleration sensor 17, and the Z-acceleration sensor 18, and then converts the voltage signals into digital signals. The sensor drive section 15 is connected to the processing section 7, and outputs the data representing the acceleration to the CPU 8 and the memory 9 via the data bus 14. The data representing the acceleration is referred to as a body motion signal.

When the user 4 performs exercise such as swimming, the user 4 moves a hand. On this occasion, the body motion sensor 10 is moved due to the motion of the hand. When the body motion sensor 10 is moved, the acceleration is applied to the body motion sensor 10. Then, the body motion sensor 10 detects the acceleration generated due to the motion of the hand. In such a manner, the body motion sensor 10 detects the body motion signal based on the motion of the user 4, and then outputs the body motion signal to the processing section 7.

The timing section 11 measures the elapse of time. The timing section 11 measures the current time. In addition, the timing section 11 measures the exercise time for which the user 4 performs the exercise. In addition, the timing section 11 measures the rest time for which the user 4 takes a rest. The timing section 11 is provided with an oscillation circuit having a quartz crystal vibrator, and a frequency divider circuit for decreasing the frequency of an oscillation waveform. Therefore, the timing section 11 is capable of accurately measuring the time by 1/100 second.

The operation section 12 can be formed of, for example, a single pushbutton 5, or a plurality of push buttons 5. The plurality of push buttons 5 is respectively assigned with instruction contents issued when being pressed. For example, the user 4 presses predetermined one of the push buttons 5 in order to make the instruction of starting the measurement of the rest time. The operation of pressing this pushbutton 5 is defined as a rest start instruction operation. The rest start instruction operation is an operation for instructing to start the rest. Then, the operation section 12 receives the rest start instruction operation of the user 4, and then outputs a rest start signal representing the start of the rest to the processing section 7. The rest start signal is a signal for making an instruction of starting the measurement of the rest time.

In addition, for example, the user 4 presses predetermined one of the push buttons 5 in order to make the instruction of terminating the measurement of the rest time. The action of pressing this push button 5 is defined as a rest termination instruction operation. The rest termination instruction operation is an operation for instructing to terminate the rest. Then, the operation section 12 receives the rest termination instruction operation of the user 4, and then outputs a rest termination signal representing the termination of the rest to the processing section 7. The rest termination signal is a signal for making an instruction of terminating the measurement of the rest time.

In addition, for example, the user 4 presses predetermined one of the push buttons 5 in order to make the instruction of starting the measurement of the exercise time. The action of pressing this push button 5 is defined as an exercise start instruction operation. The exercise start instruction operation is an operation for instructing to start the exercise. Then, the operation section 12 receives the exercise start instruction operation of the user 4, and then outputs an exercise start signal to the processing section 7. The exercise start signal is a signal for making an instruction of starting the measurement of the exercise time.

In addition, for example, the user 4 presses predetermined one of the push buttons 5 in order to make the instruction of terminating the measurement of the exercise time. The action of pressing this push button 5 is defined as an exercise termination instruction operation. The exercise termination instruction operation is an operation for instructing to terminate the exercise. Then, the operation section 12 receives the exercise termination instruction operation of the user 4, and then outputs an exercise termination signal to the processing section 7. The exercise termination signal is a signal for making an instruction of terminating the measurement of the exercise time.

In addition, for example, the user 4 presses predetermined one of the push buttons 5 in order to make an instruction of editing the measurement result of the exercise time and the measurement result of the rest time. The action of pressing this push button 5 is defined as an edit instruction operation. The edit instruction operation is an operation for instructing to start the edit. Then, the operation section 12 receives the edit instruction operation of the user 4, and then outputs an edit signal to the processing section 7. The edit signal is a signal for making an instruction of editing the measurement result of the exercise time or the rest time.

The display panel 6 displays at least the information from the timing section 11. In this information, there are included the exercise time and the rest time besides the current time. In addition, the display panel 6 displays the data indicated by the body sensor 10. In addition, when performing the swimming, the number of strokes with a hand is displayed.

The memory 9 is a concept including a semiconductor memory such as a RAM or a ROM. The memory 9 stores a program 21 in which a control procedure of the operation of the portable electronic apparatus 1 is described. In addition, the memory 9 stores acceleration data 22 representing a body motion signal of the body motion detected by the body motion sensor 10. In addition, the memory 9 stores a determination data 23 for determining whether or not a periodic component can be detected in the body motion signal. In addition, the memory 9 stores elapsed time data 24 as the data of the exercise time as the time for which the user 4 performs the exercise, the rest time for which the user 4 takes a rest, and so on. In the elapsed time data 24, there are also included the exercise start time, the exercise termination time, the rest start time, and the rest termination time. In addition, the memory 9 is provided with a storage area functioning as a work area for the CPU 8 or a temporary file, and other variety of storage areas.

The CPU 8 is for the portable electronic apparatus 1 to perform the control of measuring the exercise time and the rest time, and arithmetic processing due to the program 21 stored in the memory 9. As a specific function implementation section, there is provided a sensor control section 25. The sensor control section 25 performs the control for outputting an instruction signal to the body motion sensor 10 to drive the X-acceleration sensor 16, the Y-acceleration sensor 17, and the Z-acceleration sensor 18 to thereby obtain the body motion signal.

In addition, the CPU 8 has an analytical data forming section 26. The analytical data forming section 26 combines the body motion signal in the period from 1 second ago to the present with the body motion signal in the period from, for example, 8 seconds ago to 1 second ago to obtain the body motion signal in the period from 8 seconds ago to the present. Then, the CPU 8 performs a process of combining the body motion signals output by the respective sensors, namely the X-acceleration sensor 16, the Y-acceleration sensor 17, and the Z-acceleration sensor 18 into a single body motion signal.

In addition, the CPU 8 has a periodicity calculation section 27. The periodicity calculation section 27 performs an operation of analyzing whether or not a periodic component is included in the body motion signal. The periodicity calculation section 27 outputs a result of an analysis on whether or not the periodic component is included in the result of the analysis.

In addition, the CPU 8 has a state determination section 28. The state determination section 28 inputs the instruction signal output by the operation section 12 and the analysis result of the periodic component output by the periodicity calculation section 27. Then, the state determination section 28 performs the determination of the start of the measurement and the termination of the measurement of the exercise time using the instruction signal and the analysis result of the periodic component. Further, the determination of the start of the measurement and the termination of the measurement of the rest time is performed.

In addition, the CPU 8 has a timing data recording section 29. The timing data recording section 29 stores the measurement start time and the measurement termination time of the rest time as a part of the elapsed time data 24 in the memory 9. In addition, the timing data recording section 29 stores the time when the operation section 12 outputs the exercise start signal, the exercise termination signal, the rest start signal, and the rest termination signal to the memory 9 as a part of the elapsed time data 24.

In addition, the CPU 8 has an edit section 30. The edit section 30 inputs an edit signal from the operation section 12 to perform the edit of the exercise time and the rest time. For example, the edit section 30 inputs the edit signal from the operation section 12 to perform the edit of terminating the rest time at the time at which the rest termination signal is output. In addition, for example, the edit section 30 of the processing section 7 detects the edit signal from the operation section 12 to perform the edit of terminating the exercise time at the time at which the exercise termination signal is output.

In addition, the CPU 8 has a display control section 31. The display control section 31 extracts data in the memory 9 to form screen data to be displayed on the display panel 6. Then, the display control section 31 outputs the screen data to the display panel 6 to control the display screen of the display panel 6.

Figure 3:
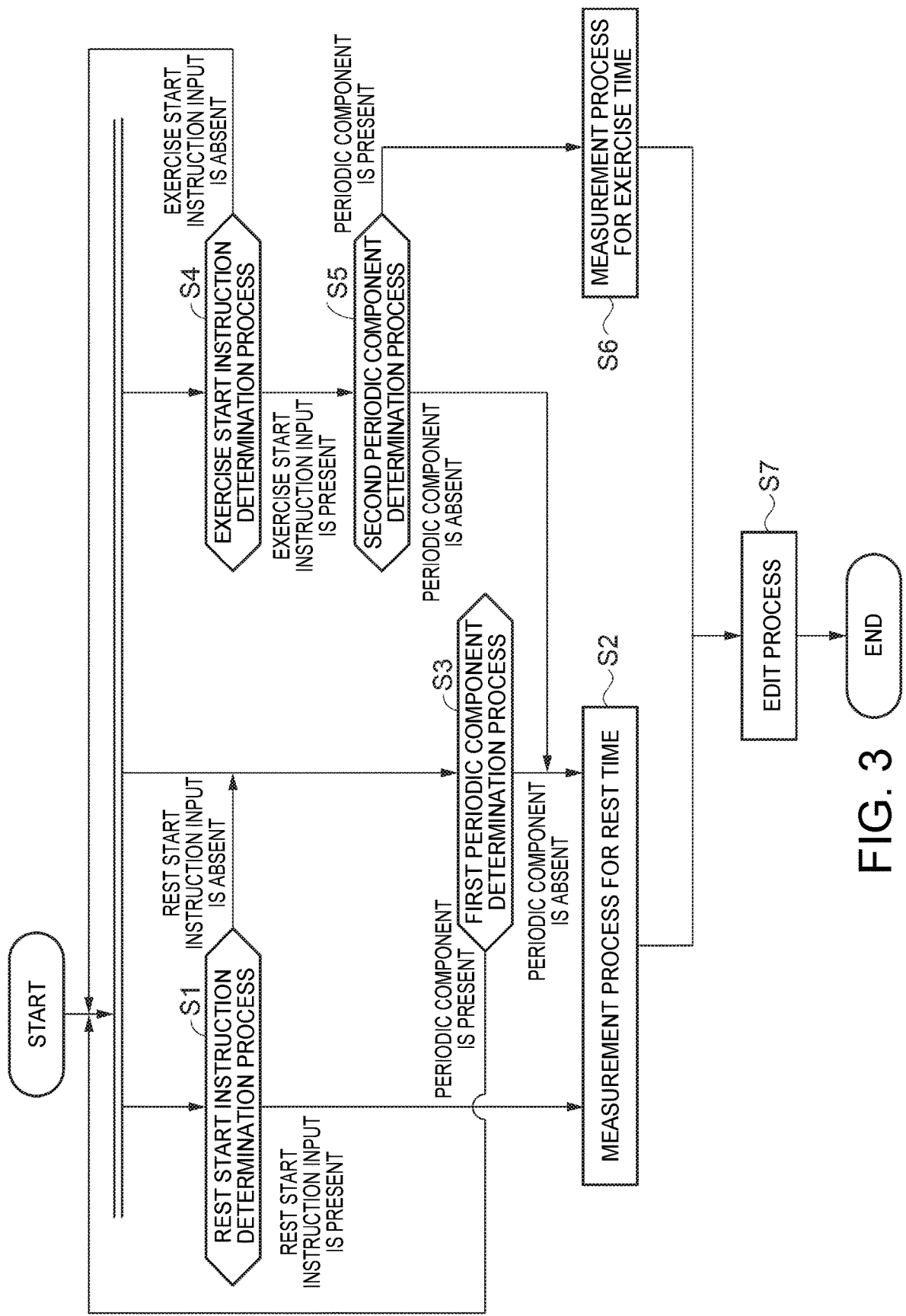
FIG. 3 is a flowchart of a time measurement method.

Then, a time measurement method for measuring the exercise time and the rest time using the portable electronic apparatus 1 described above will be described with reference to FIG. 3 through FIG. 35. FIG. 3 is a flowchart of the time measurement method, and FIG. 4 through FIG. 9 are diagrams for explaining the time measurement method. In the flowchart shown in FIG. 3, the step S1, the step S3 and the step S4 are executed in parallel to each other. The step S1 corresponds to a rest start instruction determination process. This process is a process for the state determination section 28 to determine whether or not the rest start instruction is provided from the user 4.

The rest start instruction is an instruction for starting the measurement of the rest time for which the user 4 takes a rest. In the case in which the user 4 makes the rest start instruction, by the user 4 pressing predetermined one of the push buttons 5, the operation section 12 outputs the rest start signal to the processing section 7. In the processing section 7, the timing data recording section 29 stores the time at which the rest start signal is detected to the memory 9. In the processing section 7, the state determination section 28 performs the determination on whether to start the measurement of the rest time. In the case in which the processing section 7 fails to detect the rest start signal, namely in the case in which the rest start instruction input is absent, the process makes the transition to the step S3. In the case in which the processing section 7 detects the rest start signal, namely in the case in which the rest start instruction input is present, the process makes the transition to the step S2.

The step S2 corresponds to a measurement process of the rest time. This process is a process for the timing section 11 to measure the rest time. Then, the process makes the transition to the step S7.

The step S3 corresponds to a first periodic component determination process. In this process, the processing section 7 analyzes the body motion signal output by the body motion sensor 10. Then, the periodicity calculation section 27 of the processing section 7 determines whether the periodic component based on the motion of the user 4 is detected in the body motion signal output by the body motion sensor 10, or the periodic component is not detected within a predetermined period (e.g., one of 5 seconds, 10 seconds, 30 seconds, and 60 seconds), and then the periodicity calculation section 27 outputs the determination result to the state determination section 28.

In the case in which the periodic component based on the motion of the user 4 has been detected in the body motion signal, namely in the case in which the periodic component is present, the state determination section 28 returns to the start as the next process. In the case in which the periodic component based on the motion of the user 4 has not been detected within the predetermined period, the state determination section 28 makes the transition to the step S2.

In the step S1, in the case in which the processing section 7 has detected the rest start signal, the process makes the transition to the step S2. In the case in which the processing section 7 has not detected the rest start signal, the process makes the transition to the step S3. In the step S3, in the case in which the processing section 7 has not detected the rest start signal, and has not detected the body motion signal satisfying a predetermined condition for the predetermined period, the process makes the transition to the step S2. Then, the timing section 11 starts the measurement of the rest time, and the display panel 6 displays rest information related to the rest time. The body motion signal satisfying the predetermined condition is a signal including the continuous periodic component.

In other words, in the case in which the processing section 7 has not detected the rest start signal, and has not detected the periodic component based on the motion of the user in the body motion signal for the predetermined period, the process makes the transition to the step S2 to start the measurement of the rest time by the timing section 11. Here, the rest information denotes the information including the period for which the user 4 takes a rest, the start time of the rest, and so on. Further, in the case in which the rest time and an interval distance during the workout set in advance are stored in the memory 9, it is possible to display the remaining time of the rest time or the time to the next interval as the rest information. Further, the rest information includes not only the information with text such as a number, but also the information related to the rest expressed by an object such as an icon representing the fact that the user is at rest, an object varying in accordance with elapse of time, or the combination of these objects.

Therefore, even in the case in which the user 4 forgets to make the rest instruction operation, it is possible for the portable electronic apparatus 1 to start the measurement of the rest time. Further, it is possible for the user 4 to look at the display panel 6 to check the rest information such as the time having elapsed from the start of the rest. Further, the body motion signal satisfying the predetermined condition is a signal including the continuous periodic component. Therefore, in the case in which the user 4 continuously performs repetitive motions, it is possible for the processing section 7 to detect the fact that the user 4 is doing exercise.

In the case in which the processing section 1 has not detected the rest start signal in the step S1, and has not detected the periodic component based on the motion of the user in the body motion signal for the predetermined period in the step S3, the measurement of the rest time by the timing section 11 is started. Therefore, even in the case in which the user 4 makes the operation of instructing to start the exercise, but forgets to make the operation of instructing to start the rest, it is possible for the portable electronic apparatus 1 to start the measurement of the rest time.

In the step S2, the rest information related to the rest time measured by the timing section 11 is displayed on the display panel 6. The rest information includes characters and marks representing the rest, and the elapsed time of the rest time. In the case in which predetermined rest time is set in advance, the remaining time of the rest is included in the rest information. Therefore, it is possible for the user 4 to look at the display panel 6 to check the information such as the time having elapsed from the start of the rest.

The step S4 corresponds to an exercise start instruction determination process. This process is a process for the state determination section 28 to determine whether or not the exercise start instruction is provided from the user 4. The exercise start instruction is an instruction for starting the measurement of the exercise time for which the user 4 does the exercise. In the case in which the user 4 makes the exercise start instruction, the user 4 presses predetermined one of the pushbuttons 5. The operation section 12 detects the exercise start instruction, and then outputs the exercise start signal to the processing section 7. In the processing section 7, the timing data recording section 29 stores the time at which the exercise start signal is detected to the memory 9. In the case in which the processing section 7 fails to detect the exercise start signal, namely in the case in which the exercise start instruction input is absent, the process makes the transition to the start. In the case in which the processing section 7 detects the exercise start signal, namely in the case in which the exercise start instruction input is present, the process makes the transition to the step S5.

Since the step S1 and the step S4 are executed in parallel to each other, the processing section 7 detects the rest start signal after the processing section 7 has detected the exercise start signal in some cases. In such cases, the process makes the transition to the step S2 to start the measurement of the rest time by the timing section 11. Therefore, it is possible to surely start the measurement of the rest time by the timing section 11 based on the instruction of the user 4.

The step S5 corresponds to a second periodic component determination process. In this process, the processing section 7 inputs the body motion signal output by the body motion sensor 10. Then, in the processing section 7, the periodicity calculation section 27 extracts the periodic component based on the motion of the user 4 in the body motion signal. The periodicity calculation section 27 outputs the result on whether the periodic component based on the motion of the user 4 is detected, or the periodic component based on the motion of the user 4 is not detected in a predetermined period, to the state determination section 28.

In the case in which the periodic component based on the motion of the user 4 has been detected in the body motion signal, namely in the case in which the periodic component is present, the state determination section 28 sets the step S6 as the next process to make the transition to the step S6. In the case in which the periodic component based on the motion of the user 4 has not been detected in the body motion signal for a predetermined period, the state determination section 28 sets the step S2 as the next process to make the transition to the step S2.

In the step S5, in the case in which the processing section 7 has detected the exercise start signal, and has not detected the periodic component based on the motion of the user 4 in the body motion signal for the predetermined period, the process makes the transition to the step S2 to start the measurement of the rest time by the timing section 11. Therefore, even in the case in which the user 4 makes a mistake in the operation of the operation section 12 when taking a rest, it is possible for the portable electronic apparatus 1 to start the measurement of the rest time.

The step S6 corresponds to a measurement process of the exercise time. This process is a process for the timing section 11 to measure the exercise time. Then, the process makes the transition to the step S7. The step S7 corresponds to an edit process. In this process, in the case in which the user 4 makes an operation of instructing the edit, the operation section 12 receives this operation to output the edit signal to the processing section 7. In the processing section 7, the edit section 30 detects the edit signal to perform the edit of terminating the rest time at the time at which the rest termination signal is output.

In the memory 9, there is stored the time at which the operation section 12 has output the rest termination signal. In the case in which the user 4 makes the edit instruction operation of the rest time, the operation section 12 receives the edit instruction operation of the user 4. Then, the operation section 12 outputs the edit signal to the processing section 7. The processing section 7 detects the edit signal to terminate the rest time at the time at which the rest termination signal is output. Therefore, it is possible to correct the rest time into the correct time in the case in which the rest termination signal is not caused by an erroneous operation.

Similarly, in the memory 9, there is stored the time at which the operation section 12 has output the exercise termination signal. In the case in which the user 4 makes the edit instruction operation of the exercise time, the operation section 12 receives the edit instruction operation of the user 4. Then, the operation section 12 outputs the edit signal to the processing section 7. The processing section 7 detects the edit signal to terminate the exercise time at the time at which the exercise termination signal is output. Therefore, it is possible to correct the exercise time into the correct time in the case in which the exercise termination signal is not caused by an erroneous operation. When the step S7 is completed, the process of the time measurement for measuring the exercise time is terminated. It is also possible to subsequently resume the process from the start once again. It should be noted that the edit process in the step S7 is not an essential constituent, but it is also possible to adopt a configuration of terminating the time measurement flow or returning to the start with the step S7 omitted.

Figure 4:
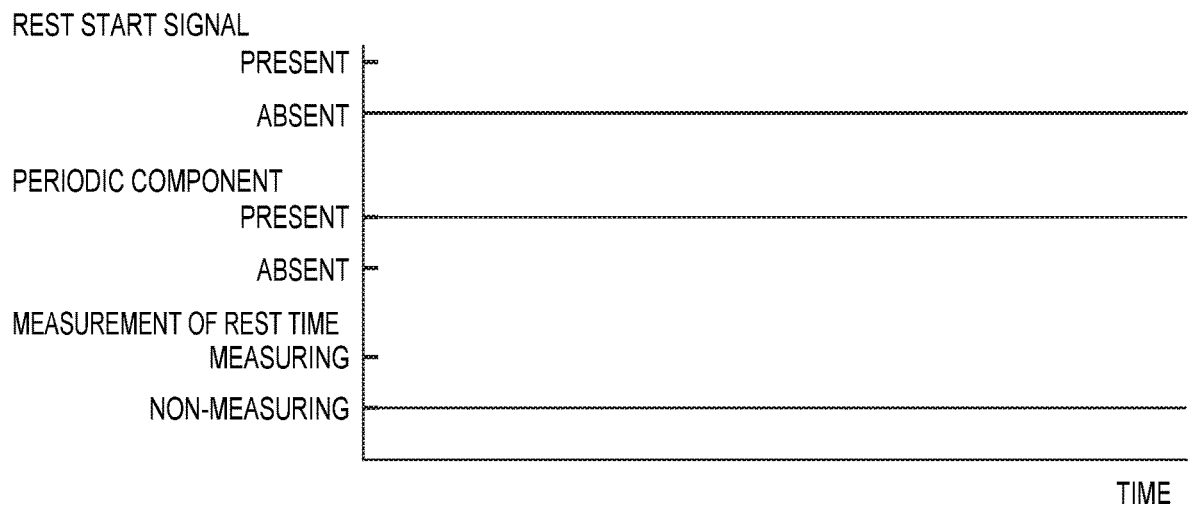
FIG. 4 is a diagram for explaining the time measurement method.
Figure 5:
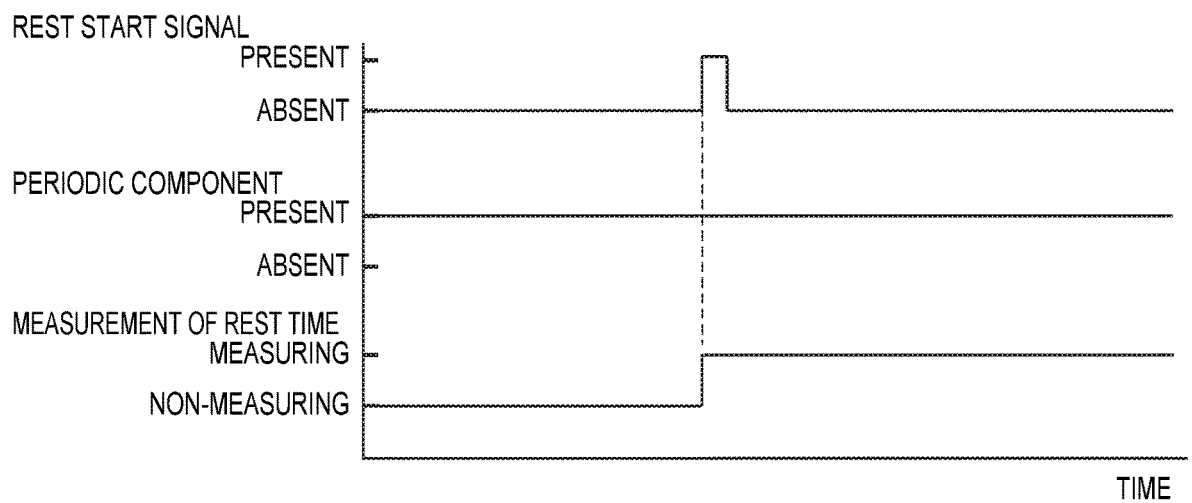
FIG. 5 is a diagram for explaining the time measurement method.
Figure 6:
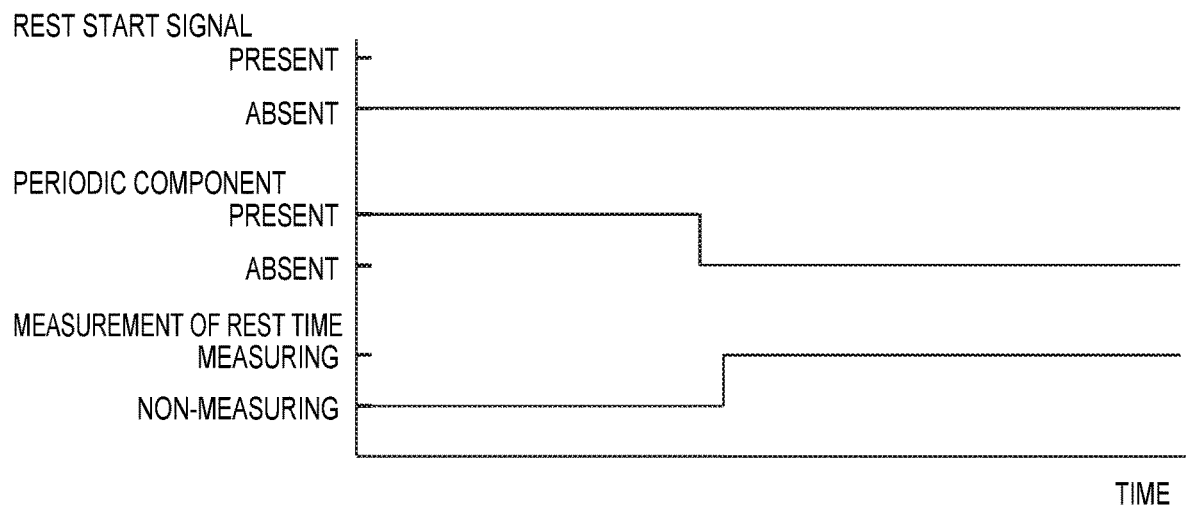
FIG. 6 is a diagram for explaining the time measurement method.

Then, the time measurement method for measuring the exercise time and the rest time will be described in detail using FIG. 4 through FIG. 9 so as to correspond to the steps shown in FIG. 3. FIG. 4 through FIG. 6 are diagrams corresponding to the rest start instruction determination process in the step S1, the measurement process of the rest time in the step S2, and the first periodic component determination process in the step S3. In FIG. 4 through FIG. 6, the horizontal axis represents the elapse of time, wherein the time elapses from the left side to the right side in each of the drawings. The vertical axis represents presence and absence of the rest start signal, presence and absence of the periodic component, and a measuring state and a non-measuring state regarding the measurement of the rest time.

As shown in FIG. 4, in the case in which the periodic component based on the motion of the user 4 is detected in the body motion signal in the absence state of the rest start signal, the process returns from the step S1 to the start via the step S3. Then, the rest time becomes in the non-measuring state.

As shown in FIG. 5, when the rest start signal turns to the presence state, the process makes the transition from the step S1 to the step S2. Then, the measurement of the rest time is started. On this occasion, also when the periodic component based on the motion of the user 4 is detected in the body motion signal, the measurement of the rest time is started.

As shown in FIG. 6, in the case in which the periodic component based on the motion of the user 4 stops to be detected in the body motion signal in the absence state of the rest start signal, the process makes the transition from the step S1 to the step S2 via the step S3. Then, the measurement of the rest time is started.

When the user 4 takes a rest, a repetitive motion is not performed for a predetermined period. When the processing section 7 fails to detect the periodic component based on the motion of the user 4 in the body motion signal for the predetermined period, the processing section 7 makes the timing section 11 start the measurement of the rest time. Then, the timing section 11 starts the measurement of the rest time. Therefore, even in the case in which the user 4 forgets to operate the operation section 12 when taking a rest, it is possible for the portable electronic apparatus 1 to start the measurement of the rest time.

Figure 7:
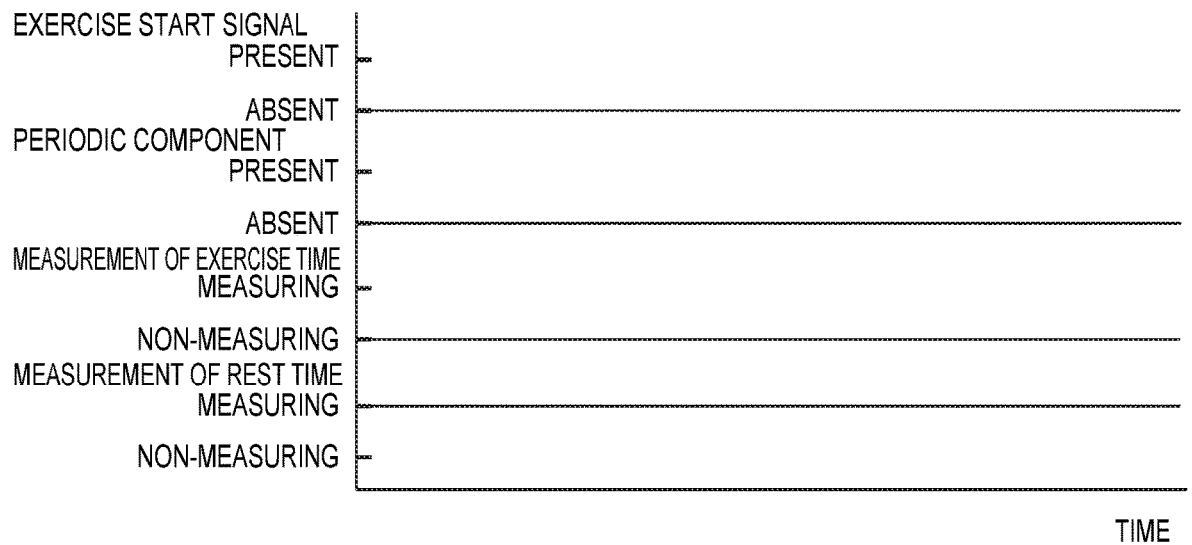
FIG. 7 is a diagram for explaining the time measurement method.
Figure 8:
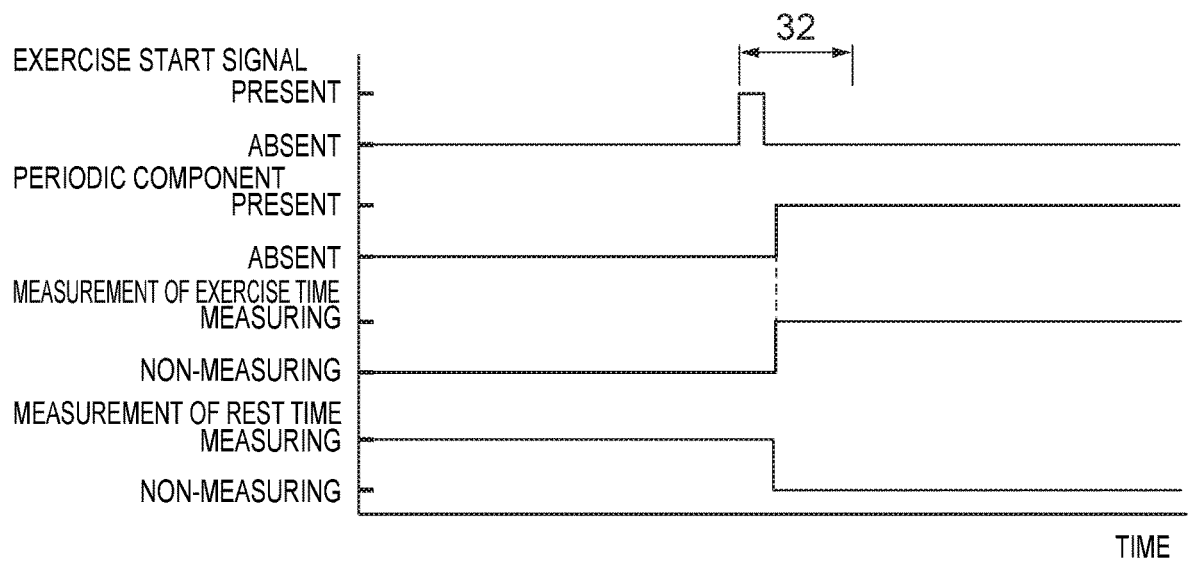
FIG. 8 is a diagram for explaining the time measurement method.
Figure 9:
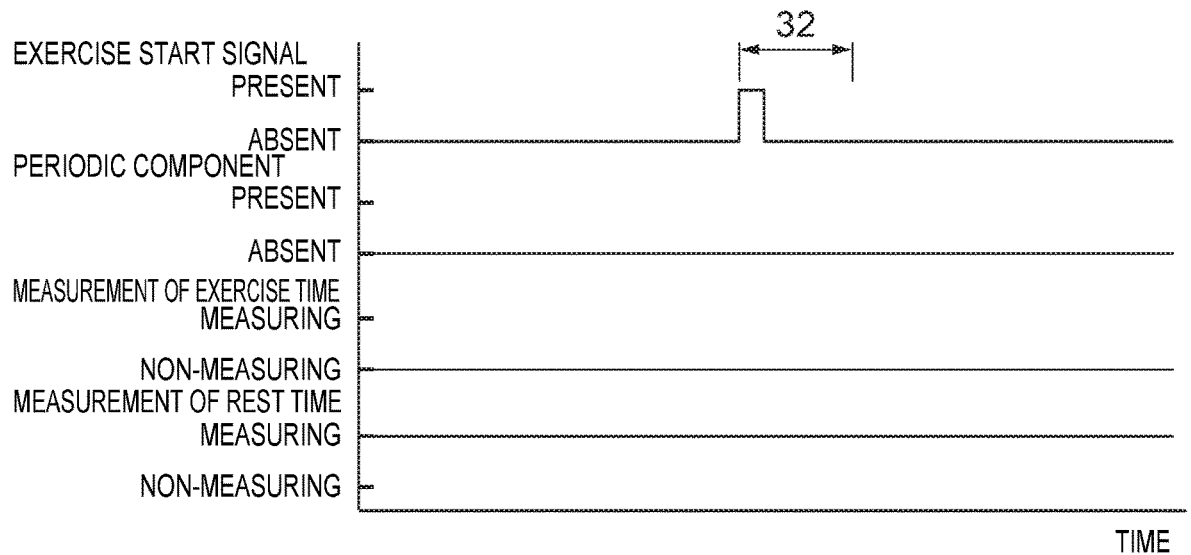
FIG. 9 is a diagram for explaining the time measurement method.

FIG. 7 through FIG. 9 are diagrams corresponding to the exercise start instruction determination process in the step S4, the second periodic component determination process in the step S5, and the measurement process of the exercise time in the step S6. In FIG. 7 through FIG. 9, the horizontal axis represents the elapse of time, wherein the time elapses from the left side to the right side in each of the drawings. The vertical axis represents presence and absence of the exercise start signal, presence and absence of the periodic component, a measuring state and a non-measuring state of the exercise time, and a measuring state and a non-measuring state regarding the measurement of the rest time.

As shown in FIG. 7, in the case in which the periodic component based on the motion of the user 4 is not detected in the body motion signal in the absence state of the exercise start signal, the process repeats the step S4. Then, the exercise time becomes in the non-measuring state. Then, the rest time becomes in the measuring state.

As shown in FIG. 8, when the exercise start signal turns to the presence state, the process makes the transition from the step S4 to the step S5. Then, when the periodic component based on the motion of the user 4 is detected in the body motion signal within a first period 32 as a predetermined period, the process makes the transition to the step S6 to start the measurement of the exercise time. The measurement of the rest time is terminated, and the rest time turns to the non-measuring state.

As shown in FIG. 9, when the exercise start signal turns to the presence state, the process makes the transition from the step S4 to the step S5. Then, in the case in which the periodic component based on the motion of the user 4 is not detected in the body motion signal within the first period 32 as the predetermined period, the process makes the transition to the step S2 to continue the non-measuring state of the measurement of the exercise time. The measurement of the rest time continues to be in the measuring state.

Figure 10:
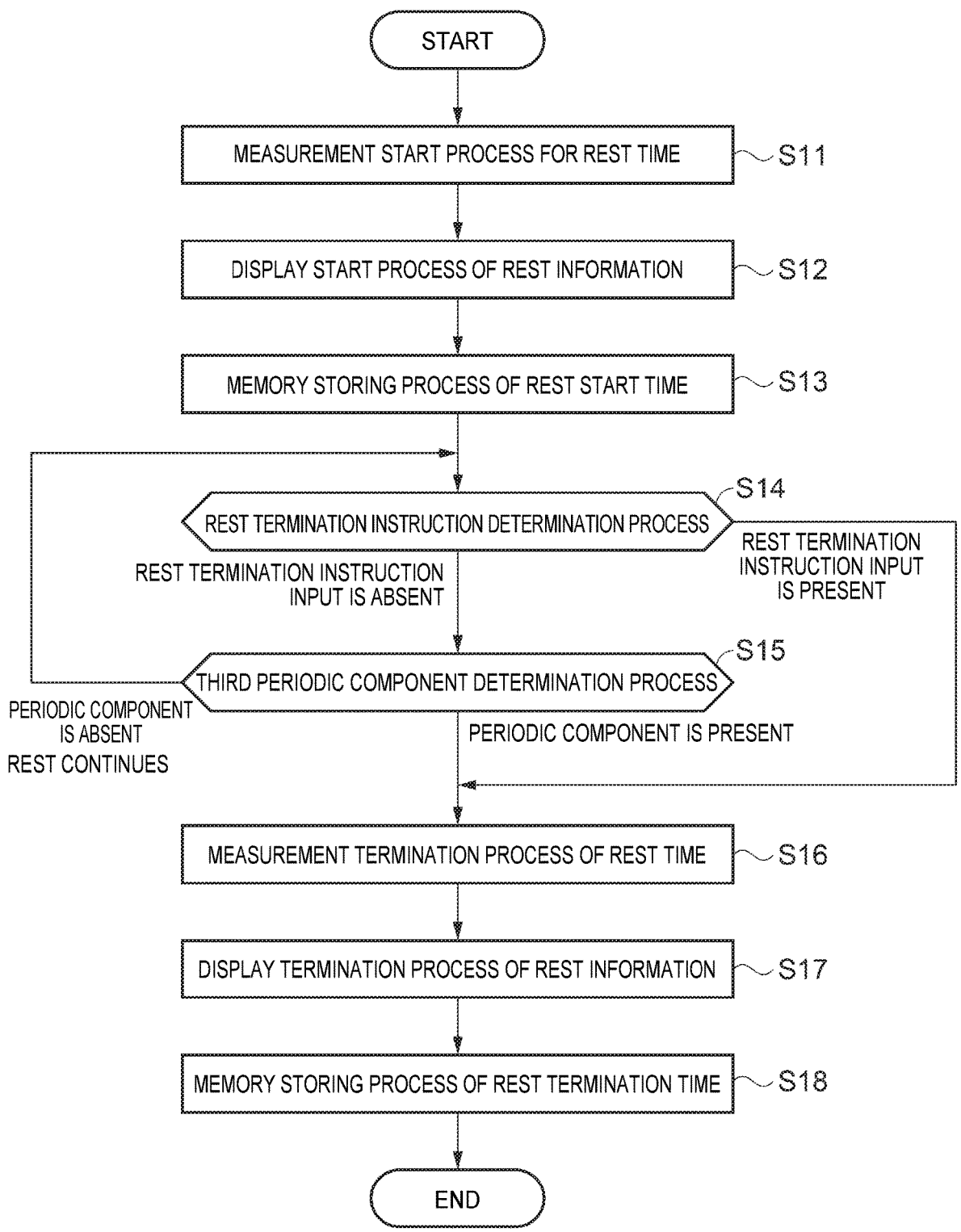
FIG. 10 is a flowchart of a measurement process of rest time.

FIG. 10 is a flowchart of the measurement process of the rest time, and a chart showing the measurement process of the rest time in the step S2 in detail. FIG. 11 through FIG. 16 are diagrams for explaining the measurement process of the rest time. The step S11 corresponds to a measurement start process of the rest time. This process is a process for the timing section 11 to start the measurement of the rest time. The timing section 11 measures the current time. Further, the timing section 11 measures the rest time. In the case in which the rest termination time is set in advance, the timing section 11 performs the calculation of the remaining time to the rest termination time.

Then, the process proceeds to the step S12. The step S12 corresponds to a display start process of the rest information. This process is a process for the display panel 6 to display the rest information related to the rest time. When the timing section 11 measures the rest time, the rest information representing the rest time is displayed on the display panel 6. Then, the process makes the transition to the step S13. The step S13 corresponds to a memory storing process of the rest start time. This process is a process for storing the time at which the rest is started to the memory 9. Then, the process makes the transition to the step S14.

The step S14 corresponds to a rest termination instruction determination process. This process is a process for the state determination section 28 to determine whether or not the rest termination instruction is provided from the user 4.

The rest termination instruction is an instruction for terminating the measurement of the rest time for which the user 4 takes a rest. In the case in which the user 4 makes the rest termination instruction, the user 4 presses predetermined one of the pushbuttons 5. The operation section 12 detects the rest termination instruction, and then outputs the rest termination signal to the processing section 7. In the processing section 7, the timing data recording section 29 stores the time at which the rest termination signal is detected to the memory 9. In the processing section 7, the state determination section 28 performs the determination on whether to terminate the measurement of the rest time. In the case in which the processing section 7 fails to detect the rest termination signal, namely in the case in which the rest termination instruction input is absent, the process makes the transition to the step S15. In the case in which the processing section 7 detects the rest termination signal, namely in the case in which the rest termination instruction input is present, the process makes the transition to the step S16.

The step S15 corresponds to a third periodic component determination process. In this process, the processing section 7 inputs the body motion signal output by the body motion sensor 10. Then, in the processing section 7, the periodicity calculation section 27 extracts the periodic component based on the motion of the user 4 in the body motion signal. The periodicity calculation section 27 outputs the result on whether the periodic component based on the motion of the user 4 is not detected, or the periodic component based on the motion of the user 4 is detected in a predetermined period, to the state determination section 28.

In the case in which the periodic component based on the motion of the user 4 has not been detected in the body motion signal, namely in the case in which the user 4 continues to take a rest, and the periodic component is absent, the state determination section 28 sets the step S14 as the next process to make the transition to the step S14. In the case in which the periodic component based on the motion of the user 4 is detected in the body motion signal for the predetermined period, the state determination section 28 sets the step S16 as the next process to make the transition to the step S16.

The step S16 corresponds to a measurement termination process of the rest time. This process is a process for the timing section 11 to terminate the measurement of the rest time. Then, the process makes the transition to the step S17. The step S17 corresponds to a display terminate process of the rest information. This process is a process for the display panel 6 to terminate the display of the rest information related to the rest time. Then, the process makes the transition to the step S18. The step S18 corresponds to a memory storing process of the rest termination time. This process is a process for the timing data recording section 29 to store the time at which the rest is terminated to the memory 9. With the steps described above, the measurement process of the rest time is terminated.

Figure 11:
FIG. 11 is a diagram for explaining the measurement process of the rest time.
Figure 12:
FIG. 12 is a diagram for explaining the measurement process of the rest time.

FIG. 11 and FIG. 12 are diagrams corresponding to the display start process of the rest time in the step S12. In the step S12, the measurement information related to the rest time is displayed on the display panel 6. FIG. 11 and FIG. 12 each show a display example of the measurement information related to the rest time shown on the display panel. As shown in FIG. 11, on the display panel 6, there are displayed the current time 33, the rest start time 34, the elapsed time 35, and rest characters 36. The elapsed time 35 represents an amount of time from the rest start time 34 to the current time 33. The elapsed time 35 increases with time. The rest characters 36 are an example of the characters representing the rest state. In addition, it is also possible to graphically display the rest information.

In the case in which the timing section 11 measures the rest time, the display panel 6 displays information of the elapsed time 35 representing the rest time as the rest information. Therefore, it is possible for the user 4 to look at the display panel 6 to check the time having elapsed from the start of the rest.

As shown in FIG. 12, on the display panel 6, there are displayed the current time 33, the rest termination setting time 37, the remaining time 38 to the termination, and the rest characters 36. The rest termination setting time 37 is the time set by the user 4, and the scheduled time at which the rest will be terminated. The remaining time 38 to the termination represents an amount of time from the current time 33 to the rest termination setting time 37. The remaining time 38 to the termination decreases with time. In the memory storing process of the rest start time in the step S13, the timing data recording section 29 stores the rest start time to the memory 9.

Figure 13:
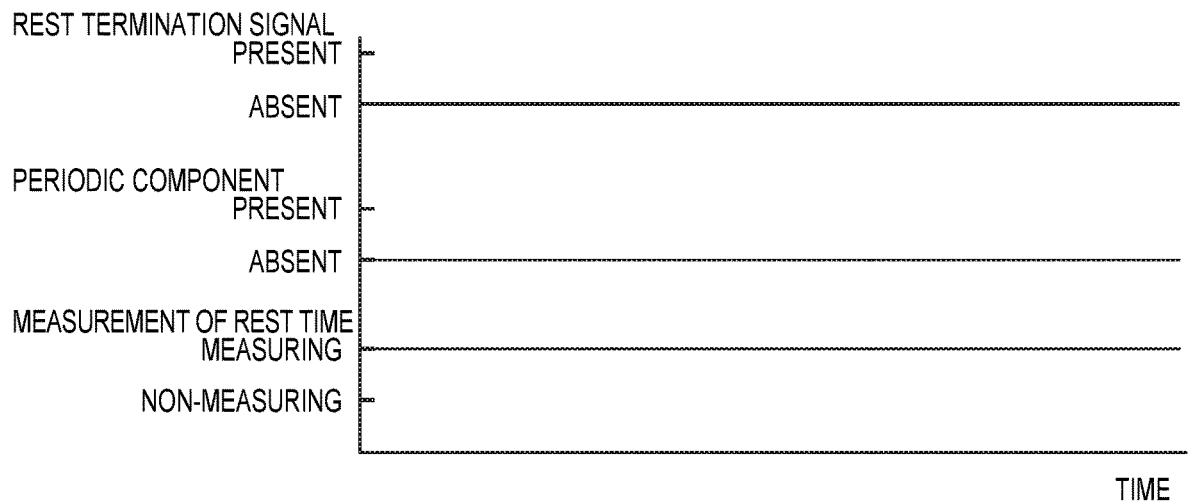
FIG. 13 is a diagram for explaining the measurement process of the rest time.
Figure 14:
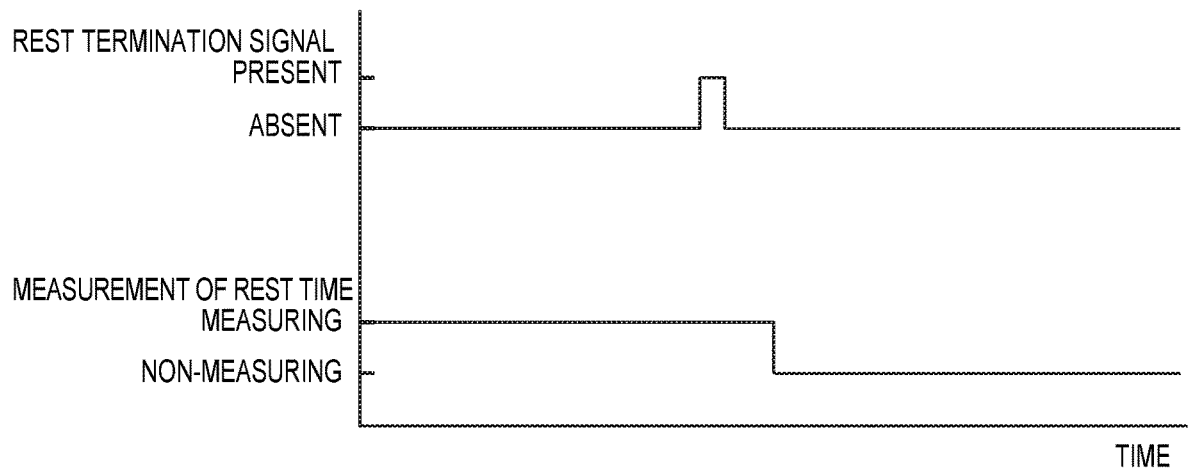
FIG. 14 is a diagram for explaining the measurement process of the rest time.
Figure 15:
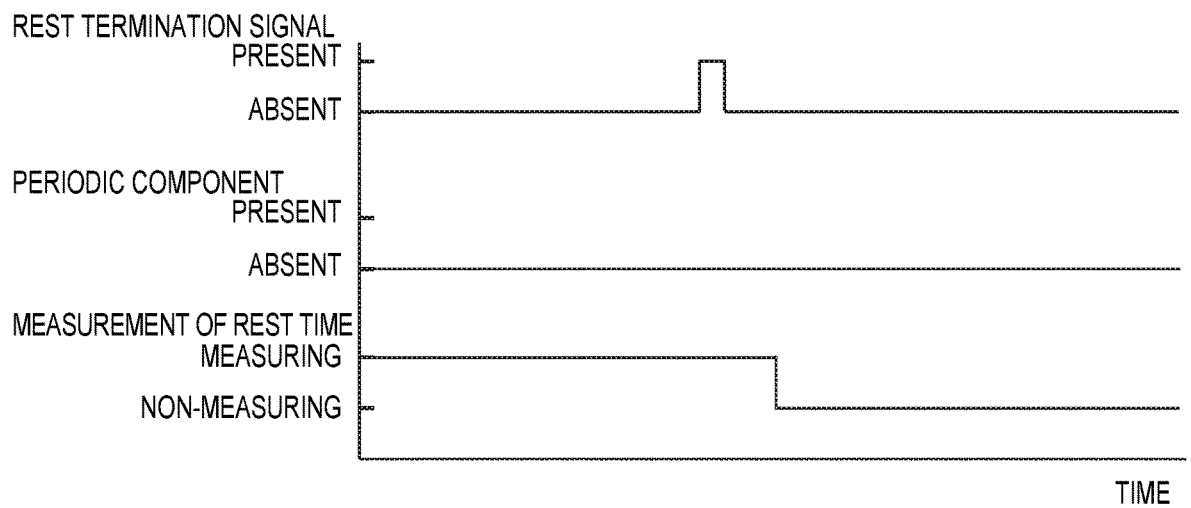
FIG. 15 is a diagram for explaining the measurement process of the rest time.

FIG. 13 through FIG. 16 are diagrams corresponding to the rest termination instruction determination process in the step S14, the third periodic component determination process in the step S15, and the measurement termination process of the rest time in the step S16. In FIG. 13 through FIG. 15, the horizontal axis represents the elapse of time, wherein the time elapses from the left side to the right side in each of the drawings. The vertical axis represents presence and absence of the rest termination signal, presence and absence of the periodic component, and a measuring state and a non-measuring state of the rest time.

As shown in FIG. 13, in the case in which the periodic component based on the motion of the user 4 is not detected in the body motion signal in the absence state of the rest termination signal, the measurement of the rest time is in the measuring state. In the case in which the rest termination signal is absent, the process makes the transition from the step S14 to the step S15. In the case in which the user 4 continues to take a rest, and the periodic component based on the motion of the user is absent in the body motion signal, the process makes the transition to the step S14.

As shown in FIG. 14, when the rest termination signal turns to the presence state, the process makes the transition from the step S14 to the step S16. Then, the measurement of the rest time by the timing section 11 is terminated. The measurement of the rest time turns to the non-measuring state.

As shown in FIG. 15, when the rest termination signal turns to the presence state, the process makes the transition from the step S14 to the step S16. In the case in which the periodic component based on the motion of the user 4 is not detected in the body motion signal after the measurement of the rest time is started, the measurement of the rest time by the timing section 11 is also terminated. Then, the measurement of the rest time turns to the non-measuring state.

Figure 16:
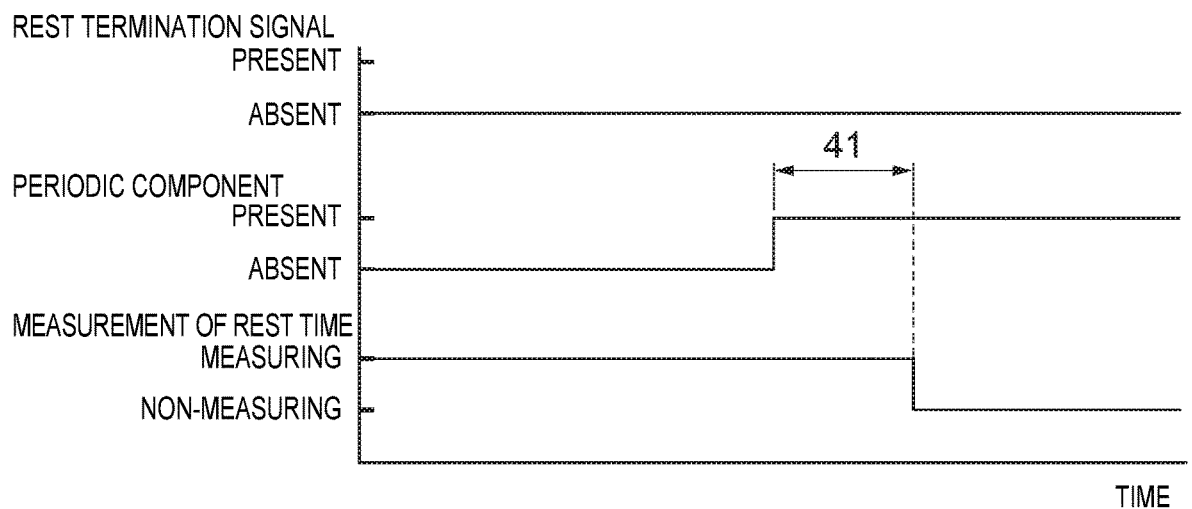
FIG. 16 is a diagram for explaining the measurement process of the rest time.

As shown in FIG. 16, when the rest termination signal is absent, the process makes the transition from the step S14 to the step S15. In the case in which the periodic component based on the motion of the user 4 is detected in the body motion signal for a second period 41 as the predetermined period after the measurement of the rest time is started, the measurement of the rest time by the timing section 11 is terminated. Then, the measurement of the rest time turns to the non-measuring state. Therefore, even in the case in which the user 4 forgets to operate the operation section 12, it is possible to terminate the measurement of the rest time.

In the measurement termination process of the rest time in the step S16, the timing section 11 terminates the measurement of the rest time. In the display termination process of the rest time in the step S17, switching of the display of the elapsed time 35 and the remaining time 38 to the termination is stopped. In other words, the values represented by the elapsed time 35 and the remaining time 38 to the termination do not vary. In the memory storing process of the rest termination time in the step S18, the timing data recording section 29 stores the time at which the rest is terminated to the memory 9.

Figure 17:
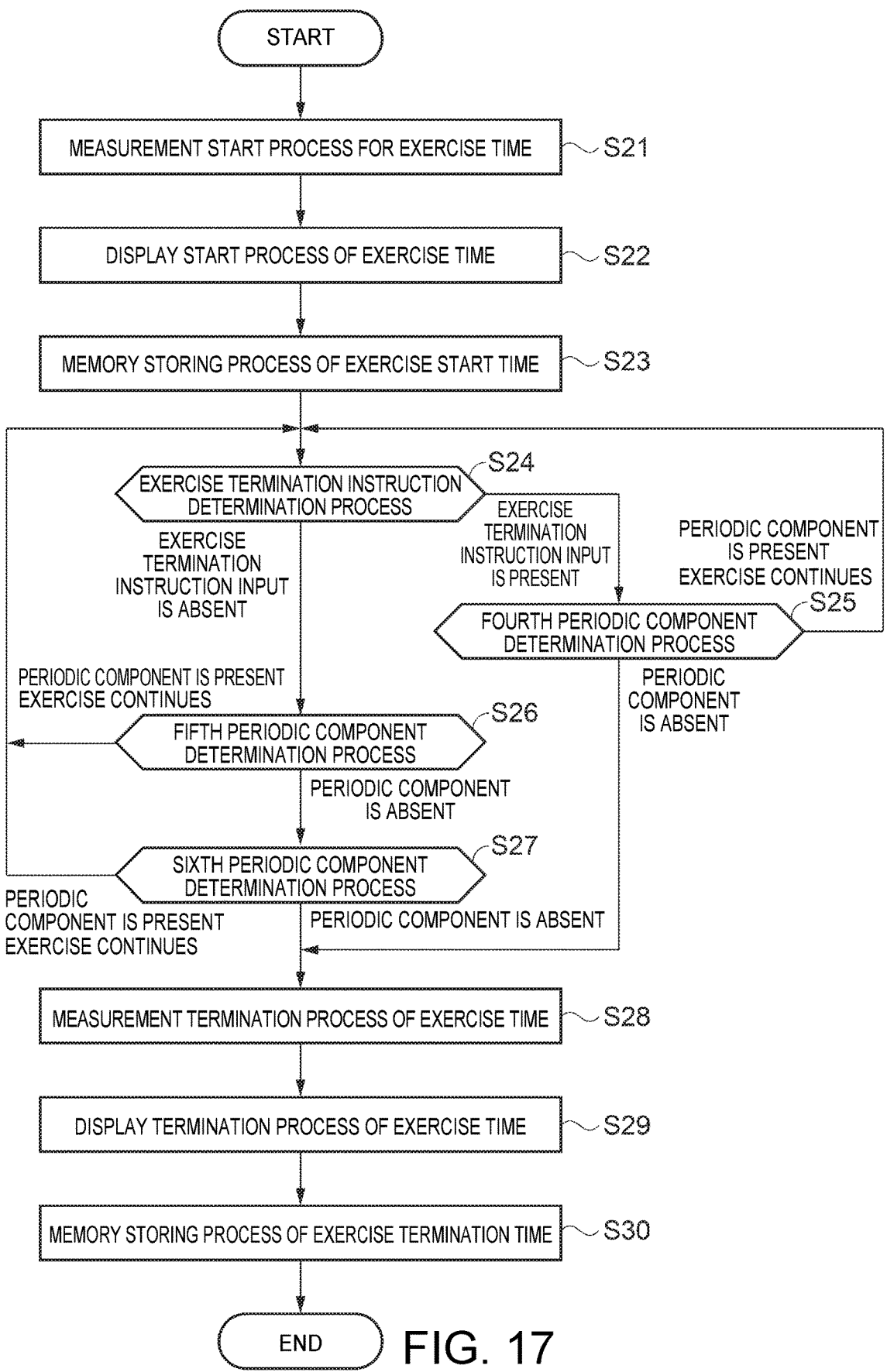
FIG. 17 is a flowchart of a measurement process of exercise time.

FIG. 17 is a flowchart of the measurement process of the exercise time, and FIG. 18 through FIG. 23 are diagrams for explaining the measurement process of the exercise time. The step S21 corresponds to a measurement start process of the exercise time. This process is a process for the timing section 11 to start the measurement of the exercise time. The timing section 11 measures the current time. Further, the timing section 11 measures the exercise time. In the case in which scheduled exercise termination time is set in advance, the timing section 11 performs the calculation of the remaining time to the scheduled exercise termination time.

Then, the process makes the transition to the step S22. The step S22 corresponds to a display start process of the exercise time. This process is a process for the display panel 6 to display the measurement information related to the exercise time. Then, the process makes the transition to the step S23. The step S23 corresponds to a memory storing process of the exercise start time. This process is a process for the timing data recording section 29 to store the time at which the exercise is started to the memory 9. Then, the process makes the transition to the step S24.

The step S24 corresponds to an exercise termination instruction determination process. This process is a process for the state determination section 28 to determine whether or not the exercise termination instruction is provided from the user 4.

The exercise termination instruction is an instruction for terminating the measurement of the exercise time for which the user 4 does the exercise. In the case in which the user 4 makes the exercise termination instruction, the user 4 presses predetermined one of the push buttons 5. The operation section 12 detects the exercise termination instruction, and then outputs the exercise termination signal to the processing section 7. In the processing section 7, the exercise termination signal is detected, and the timing data recording section 29 stores the exercise termination time to the memory 9. Then, in the processing section 7, the state determination section 28 performs the determination on whether to terminate the measurement of the exercise time. In the case in which the processing section 7 fails to detect the exercise termination signal, namely in the case in which the exercise termination instruction input is absent, the process makes the transition to the step S26. In the case in which the processing section 7 detects the exercise termination signal, namely in the case in which the exercise termination instruction input is present, the process makes the transition to the step S25.

The step S25 corresponds to a fourth periodic component determination process. In this process, the processing section 7 inputs the body motion signal output by the body motion sensor 10. Then, in the processing section 7, the periodicity calculation section 27 extracts the periodic component based on the motion of the user 4 in the body motion signal. The periodicity calculation section 27 outputs the result on whether the periodic component based on the motion of the user 4 is not detected, or the periodic component based on the motion of the user 4 is detected for a predetermined period, to the state determination section 28.

In the case in which the periodic component based on the motion of the user 4 is detected in the body motion signal, namely in the case in which the user 4 continues the exercise, and the periodic component is present, the state determination section 28 sets the step S24 as the next process to make the transition to the step S24. In the case in which the periodic component based on the motion of the user 4 is not detected in the body motion signal for a predetermined period, the state determination section 28 sets the step S28 as the next process to make the transition to the step S28.

The step S26 corresponds to a fifth periodic component determination process. In this process, the processing section 7 inputs the body motion signal output by the body motion sensor 10. Then, in the processing section 7, the periodicity calculation section 27 extracts the periodic component based on the motion of the user 4 in the body motion signal. The periodicity calculation section 27 outputs the result on whether the periodic component based on the motion of the user 4 is not detected, or the periodic component based on the motion of the user 4 is detected for a predetermined period, to the state determination section 28.

In the case in which the periodic component based on the motion of the user 4 is detected in the body motion signal, namely in the case in which the user 4 continues the exercise, and the periodic component is present, the state determination section 28 sets the step S24 as the next process to make the transition to the step S24. In the case in which the periodic component based on the motion of the user 4 is not detected in the body motion signal, the state determination section 28 sets the step S27 as the next process to make the transition to the step S27.

The step S27 corresponds to a sixth periodic component determination process. In this process, the processing section 7 inputs the body motion signal output by the body motion sensor 10 for a predetermined period. Then, in the processing section 7, the periodicity calculation section 27 extracts the periodic component based on the motion of the user 4 in the body motion signal. The periodicity calculation section 27 outputs the result on whether the periodic component based on the motion of the user 4 is not detected, or the periodic component based on the motion of the user 4 is detected for a predetermined period, to the state determination section 28.

In the case in which the periodic component based on the motion of the user 4 is detected in the body motion signal within the predetermined period, namely in the case in which the user 4 continues the exercise, and the periodic component is present, the state determination section 28 sets the step S24 as the next process to make the transition to the step S24. On this occasion, even in the case in which the user 4 stops the exercise for a short period of time, if the exercise stop time is within a predetermined period, the state determination section 28 sets the step S24 as the next process to make the transition to the step S24. In the case in which the periodic component based on the motion of the user 4 is not detected in the body motion signal for the predetermined period, the state determination section 28 sets the step S28 as the next process to make the transition to the step S28.

In the case in which the periodic component is detected within the predetermined time in the step S27 after the processing section 7 has turned to the state of not detecting the periodic component while the timing section 11 is measuring the exercise time in the step S26, the process makes the transition to the step S24. Then, the timing section 11 continues the measurement of the exercise time.

In the case in which the user 4 makes the repetitive motion, the timing section 11 measures the exercise time for which the user 4 does the exercise. In the case in which the user 4 stops the repetitive motion, the processing section 7 turns to the state of not detecting the periodic component. In the case in which the user 4 resumes the repetitive motion within a predetermined period, the processing section 7 detects the periodic component within the predetermined period after the processing section 7 has turned to the state of not detecting the periodic component. On this occasion, the processing section 7 makes the timing section 11 continue the measurement of the exercise time. Therefore, in the case in which the user 4 resumes the repetitive motion after once stopping the repetitive motion within the predetermined period, the timing section 11 continuously measures the exercise time. For example, in some cases, the user 4 makes a turn at the wall of a swimming pool, and then proceeds for a while with the arms stretched while performing the swimming. Even on this occasion, in the case in which the user 4 makes the repetitive motion of moving the arms within the predetermined period, the timing section 11 continues the measurement of the exercise time. Therefore, even in the case in which the repetitive motion is stopped within the predetermined period during the exercise, it is possible for the user 4 to make the portable electronic apparatus 1 continue the measurement of the exercise time.

The step S28 corresponds to a measurement termination process of the exercise time. This process is a process for the timing section 11 to terminate the measurement of the exercise time. Then, the process makes the transition to the step S29. The step S29 corresponds to a display termination process of the exercise time. This process is a process for the display panel 6 to terminate the display of the measurement information related to the exercise time. Then, the process makes the transition to the step S30. The step S30 corresponds to a memory storing process of the exercise termination time. This process is a process for the timing data recording section 29 to store the time at which the exercise is terminated to the memory 9. With the steps described above, the measurement process of the exercise time is terminated.

Figure 18:
FIG. 18 is a diagram for explaining the measurement process of the exercise time.

FIG. 18 is a diagram corresponding to the display start process of the exercise time in the step S22. In the step S22, the measurement information related to the exercise time is displayed on the display panel 6. FIG. 18 shows a display example of the measurement information related to the exercise time shown on the display panel. As shown in FIG. 18, on the display panel 6, there are displayed the current time 33, the exercise start time 42, the elapsed time 43, and exercise characters 44. The elapsed time 43 represents an amount of time from the exercise start time 42 to the current time 33. The elapsed time 43 increases with time. The exercise characters 44 are an example of the characters representing the exercise state. In addition, it is also possible to graphically display the exercise state.

In addition, it is also possible to display the information such as scheduled exercise termination setting time or remaining time to the scheduled termination time on the display panel 6. The scheduled exercise termination setting time is the time set by the user 4, and the scheduled time at which the exercise will be terminated. The remaining time to the scheduled termination time represents an amount of time from the current time 33 to the scheduled exercise termination setting time. The remaining time to the termination decreases with time. In the memory storing process of the exercise start time in the step S23, the timing data recording section 29 stores the exercise start time to the memory 9.

FIG. 19 through FIG. 23 are diagrams corresponding to the exercise termination instruction determination process in the step S24 through the measurement termination process of the exercise time in the step S28. In FIG. 19 through FIG. 23, the horizontal axis represents the elapse of time, wherein the time elapses from the left side to the right side in each of the drawings. The vertical axis represents presence and absence of the exercise termination signal, presence and absence of the periodic component, and a measuring state and a non-measuring state of the exercise time.

Figure 19:
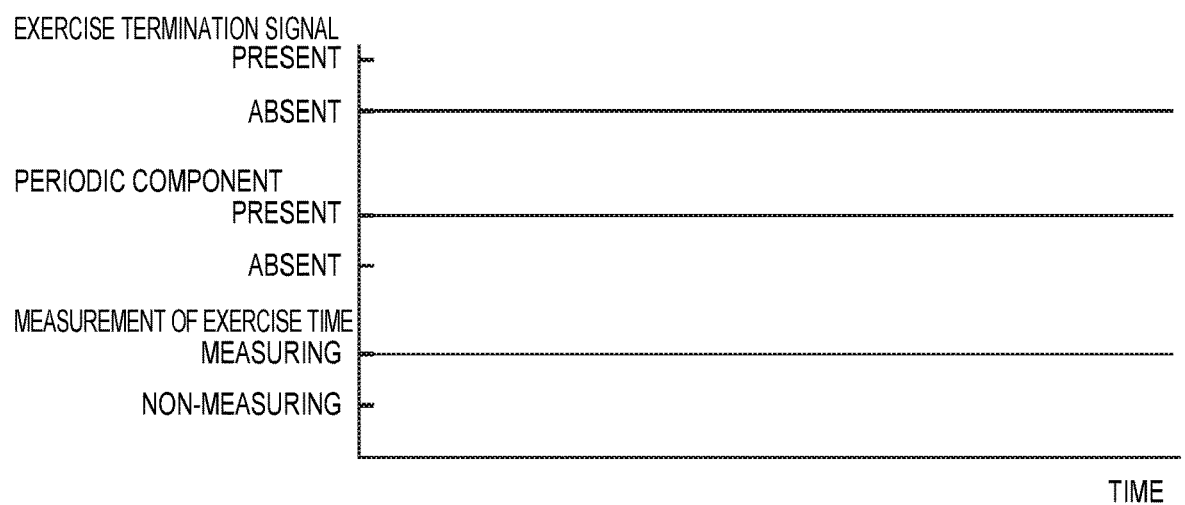
FIG. 19 is a diagram for explaining the measurement process of the exercise time.

As shown in FIG. 19, in the case in which the periodic component based on the motion of the user 4 is detected in the body motion signal in the absence state of the exercise termination signal, the measurement of the exercise time is in the measuring state. In the case in which the exercise termination signal is absent, the process makes the transition from the step S24 to the step S26. In the case in which the user 4 continues the exercise, and the periodic component based on the motion of the user is present in the body motion signal, the process makes the transition from the step S26 to the step S24.

Figure 20:
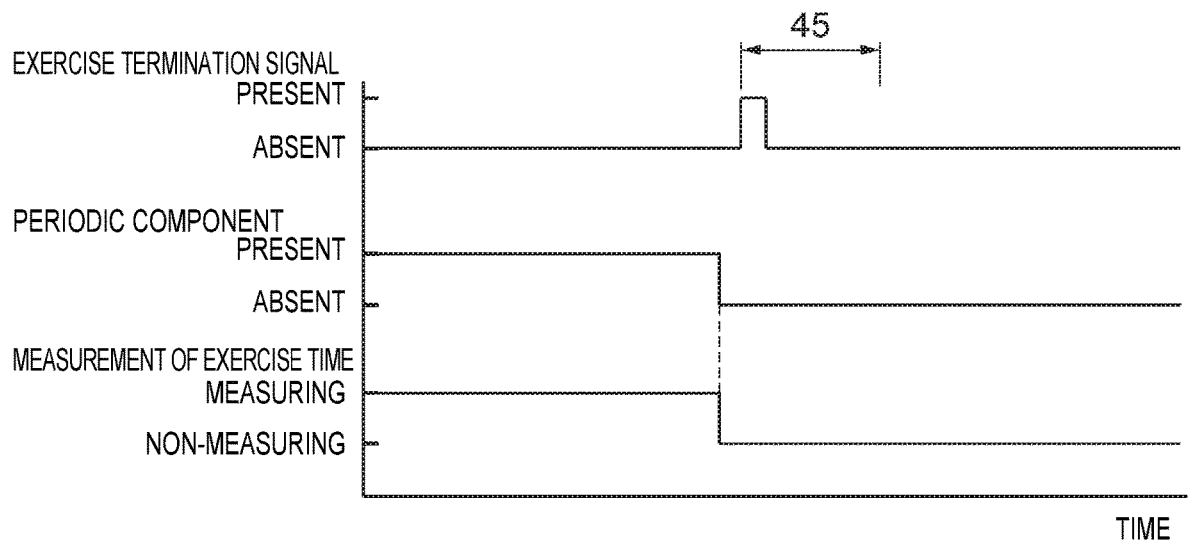
FIG. 20 is a diagram for explaining the measurement process of the exercise time.

As shown in FIG. 20, when the exercise termination signal turns to the presence state, the process makes the transition from the step S24 to the step S25. In the case in which the processing section 7 detects the exercise termination signal while the timing section 11 is measuring the exercise time, and the body motion signal including the periodic component based on the motion of the user 4 is not detected in the third period 45 as the predetermined period, the timing section 11 terminates the measurement of the exercise time. Then, the measurement of the exercise time turns to the non-measuring state.

Figure 21:
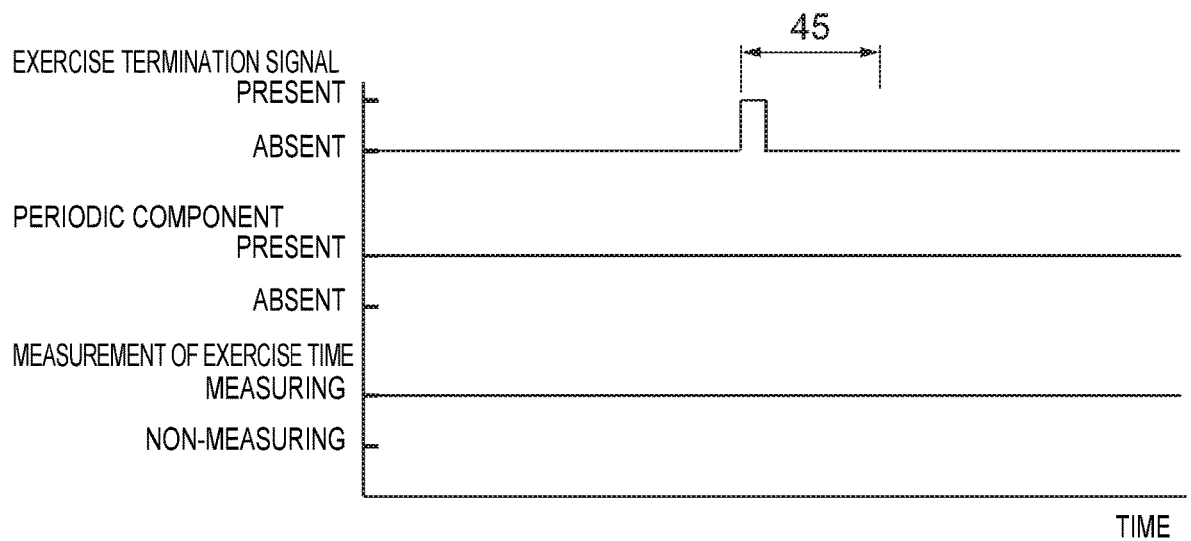
FIG. 21 is a diagram for explaining the measurement process of the exercise time.

As shown in FIG. 21, when the exercise termination signal turns to the presence state, the process makes the transition from the step S24 to the step S25. In the case in which the processing section 7 detects the exercise termination signal while the timing section 11 is measuring the exercise time, and the body motion signal including the periodic component based on the motion of the user 4 is detected in the third period 45, the timing section 11 continues the measurement of the exercise time.

In the case in which the user 4 continues the repetitive motion, and makes the exercise termination instruction operation, the timing section 11 continues the measurement of the exercise time. Therefore, in the case in which the operation of instructing the exercise termination is an erroneous operation, it is possible for the timing section 11 to continue the measurement of the exercise time. For example, in the case in which the user 4 makes a turn while performing the swimming, the push buttons 5 of the portable electronic apparatus 1 attached to the arm collide with the wall of the swimming pool in some cases. On this occasion, in the case in which the user 4 continues the swimming, the timing section 11 continues the measurement of the exercise time.

Figure 22:
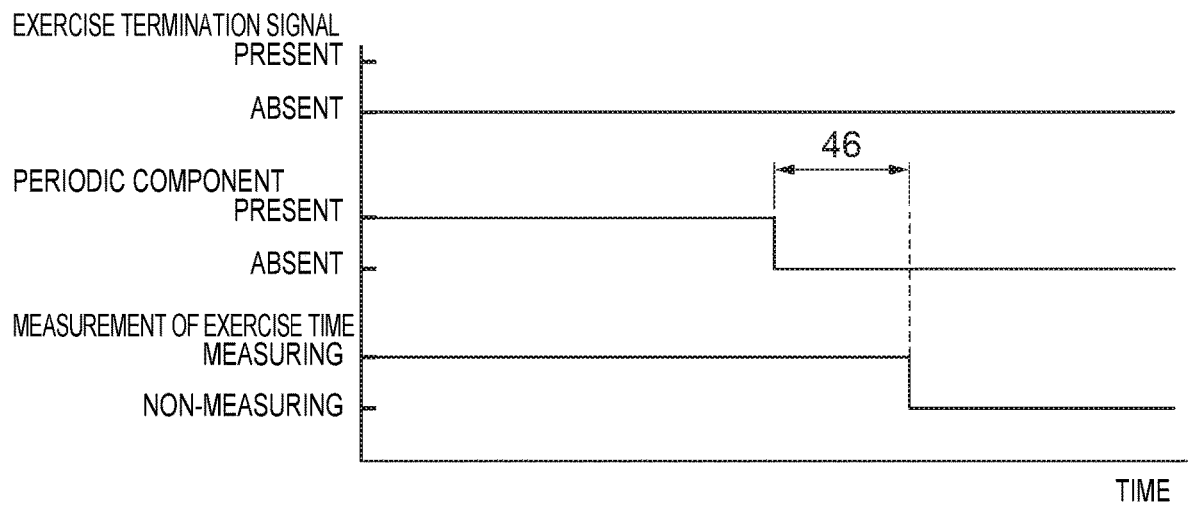
FIG. 22 is a diagram for explaining the measurement process of the exercise time.

As shown in FIG. 22, in the case in which the exercise termination signal is absent, the process makes the transition from the step S24 to the step S26. In the case in which the periodic component based on the motion of the user 4 is not detected in the body motion signal after the measurement of the exercise time is started, the process makes the transition to the step S27. In the step S27, whether or not the periodic component based on the motion of the user 4 can be detected in the fourth period 46 as the predetermined period. In the case in which the periodic component is not detected within the fourth period 46 after the processing section 7 has turned to the state of not detecting the periodic component while the timing section 11 is measuring the exercise time, the process makes the transition from the step S27 to the step S28. In the step S28, the timing section 11 terminates the measurement of the exercise time. Thus, the measurement of the exercise time turns to the non-measuring state.

Figure 23:
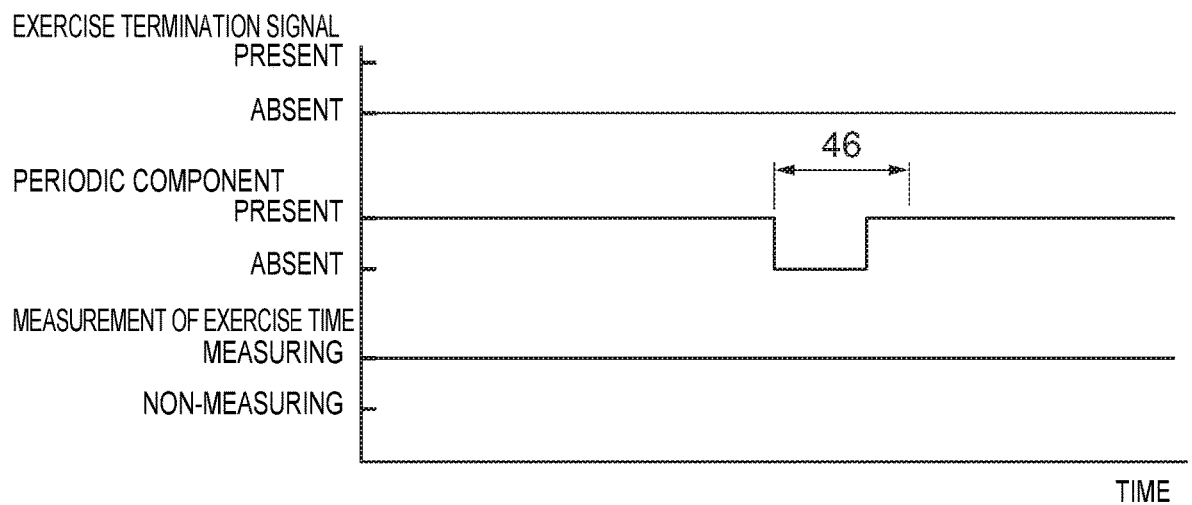
FIG. 23 is a diagram for explaining the measurement process of the exercise time.

As shown in FIG. 23, in the case in which the periodic component is detected within the fourth period 46 after the processing section 7 has turned to the state of not detecting the periodic component while the timing section 11 is measuring the exercise time, the process makes the transition from the step S27 to the step S24. Then, the timing section 11 continues the measurement of the exercise time. Thus, the measurement of the exercise time continues to be in the measuring state.

In the case in which the user 4 stops the repetitive motion, the processing section 7 turns to the state of not detecting the periodic component. In the case in which the user 4 resumes the repetitive motion within the fourth period 46, the processing section 7 detects the periodic component within the fourth period 46 after the processing section 7 has turned to the state of not detecting the periodic component. On this occasion, the processing section 7 makes the timing section 11 continue the measurement of the exercise time. Therefore, in the case in which the user 4 resumes the repetitive motion after once stopping the repetitive motion within the predetermined period, the timing section 11 continuously measures the exercise time. As a result, it is possible for the user 4 to make the portable electronic apparatus 1 continue the measurement of the exercise time.

For example, in some cases, the user 4 touches the course rope to lose a balance, and stops while performing the swimming. Even in this case, in the case in which the user resumes the swimming within the fourth period 46, the measurement of the exercise time by the timing section 11 is continued.

In the measurement termination process of the exercise time in the step S28, the timing section 11 terminates the measurement of the exercise time. In the display termination process of the exercise time in the step S29, switching of the display of the elapsed time 43 is stopped. Therefore, the value represented by the elapsed time 43 does not change. In the memory storing process of the exercise termination time in the step S30, the timing data recording section 29 of the processing section 7 stores the time at which the exercise is terminated to the memory 9. When the step S30 is completed, the measurement process of the exercise time is terminated.

Figure 24:
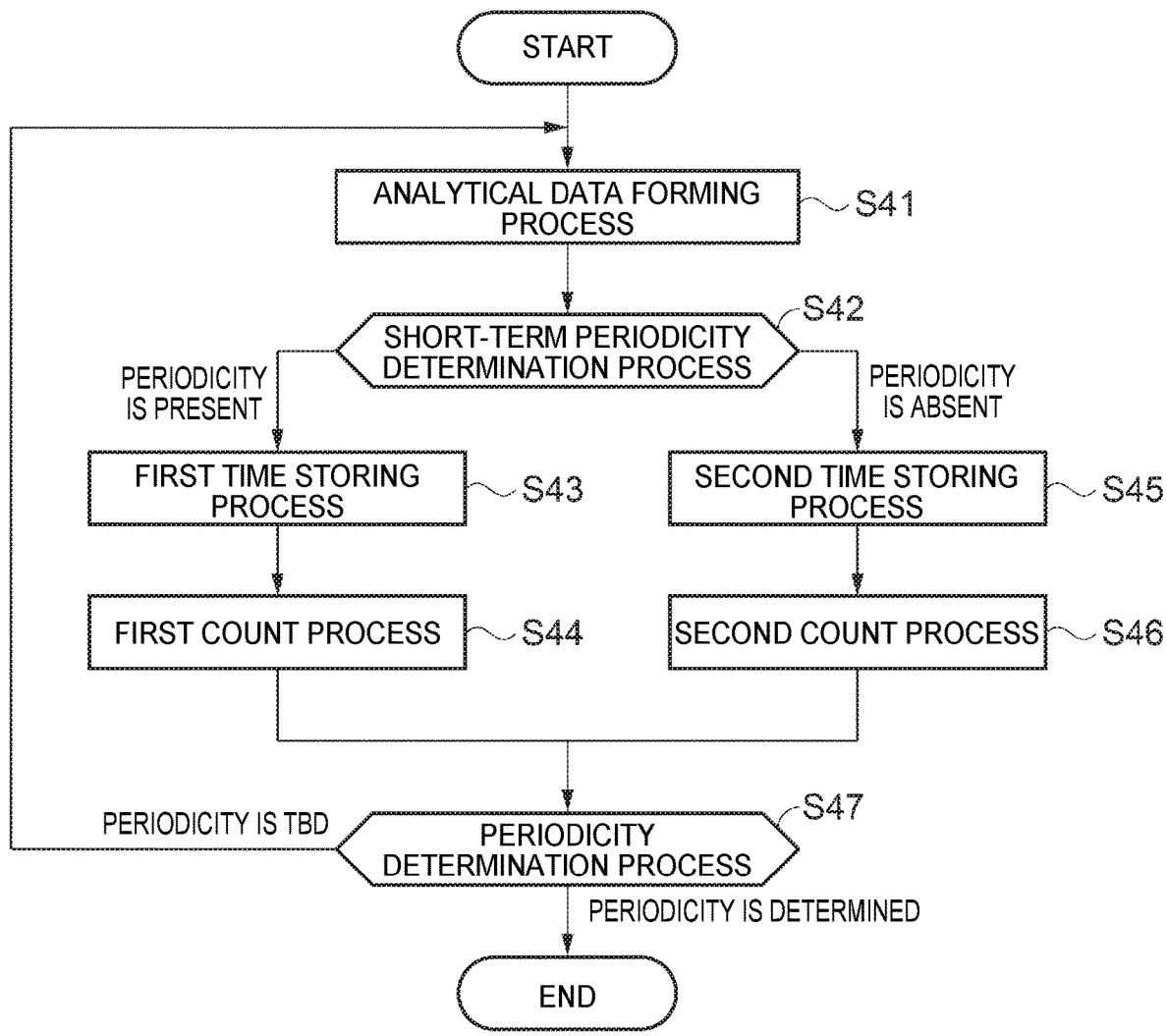
FIG. 24 is a flowchart of a periodic component determination process.

FIG. 24 is a flowchart of a periodic component determination process. The periodic component determination process includes the first periodic component determination process in the step S3, the second periodic component determination process in the step S5, the third periodic component determination process in the step S15, the fourth periodic component determination process in the step S25, the fifth periodic component determination process in the step S26, and the sixth periodic component determination process in the step S27.

The step S41 corresponds to an analytical data forming process. This process is a process for the analytical data forming section 26 to form short-term analytical data using the data of the time measured by the timing section 11. The short-term analytical data represents analytical data in a short period. The step S42 corresponds to a short-term periodicity determination process. This process is a process for determining whether or not the short-term analytical data includes the periodicity based on the motion of the user 4. In the case in which it is determined that the short-term analytical data has the periodicity, the process makes the transition to the step S43. In the case in which it is determined that the short-term analytical data has no periodicity, the process makes the transition to the step S45.

The step S43 corresponds to a first time storing process. This process is a process for the periodicity calculation section 27 to store the time at which the timing section 11 measures the short-term analytical data. The short-term analytical data is the data determined by the periodicity calculation section 27 that "the periodicity is present." Then, the process makes the transition to the step S44. The step S44 corresponds to a first count process. This process is a process for counting the number of consecutive times that the periodicity calculation section 27 determines that "the periodicity is present." The number of consecutive times of the determination that "the periodicity is present" is defined as the number of times of presence of the periodicity. Then, the process makes the transition to the step S47.

The step S45 corresponds to a second time storing process. This process is a process for storing the time at which the timing section 11 measures the short-term analytical data. The short-term analytical data is the data determined by the periodicity calculation section 27 that "the periodicity is absent." Then, the process makes the transition to the step S46. The step S46 corresponds to a second count process. This process is a process for counting the number of consecutive times that the periodicity calculation section 27 determinations that "the periodicity is absent." The number of consecutive times of the determination that "the periodicity is absent" is defined as the number of times of absence of the periodicity. Then, the process makes the transition to the step S47.

The step S47 corresponds to a periodicity determination process. This process is a process for the periodicity calculation section 27 to determine whether or not the analytical data includes the periodicity based on the motion of the user 4. In the case in which the number of times of presence of the periodicity is equal to or larger than 4, the periodicity calculation section 27 determines that "the periodicity is present" in the analytical data. Further, in the case in which the number of times of absence of the periodicity is equal to or larger than 4, the periodicity calculation section 27 determines that "the periodicity is absent" in the analytical data.

Then, in the case in which the number of times of presence of the periodicity is smaller than 4 and the number of times of absence of the periodicity is smaller than 4, the periodicity calculation section 27 determines that "the periodicity is TBD." In the case in which "the periodicity is TBD," then, the process makes the transition to the step S41. In the case in which it is determined that "the periodicity is present" or that "the periodicity is absent," the periodic component determination process is terminated.

FIG. 25 through FIG. 35 are diagrams for explaining the periodic component determination process. Then, the periodic component determination process will be described in detail using FIG. 25 through FIG. 35 so as to correspond to the steps shown in FIG. 24. In FIG. 25 through FIG. 32, the horizontal axis represents the elapse of time, wherein the time elapses from the left side to the right side in each of the drawings. The vertical axis represents the acceleration detected by the body motion sensor 10. The acceleration corresponds to the acceleration applied to the portable electronic apparatus 1 when the user 4 moves the arm. In each of the drawings, the upper side represents the + side, and the lower side represents the − side. The + side and the − side depend on the orientation of the sensor. The detailed description will be omitted.

Figure 25:
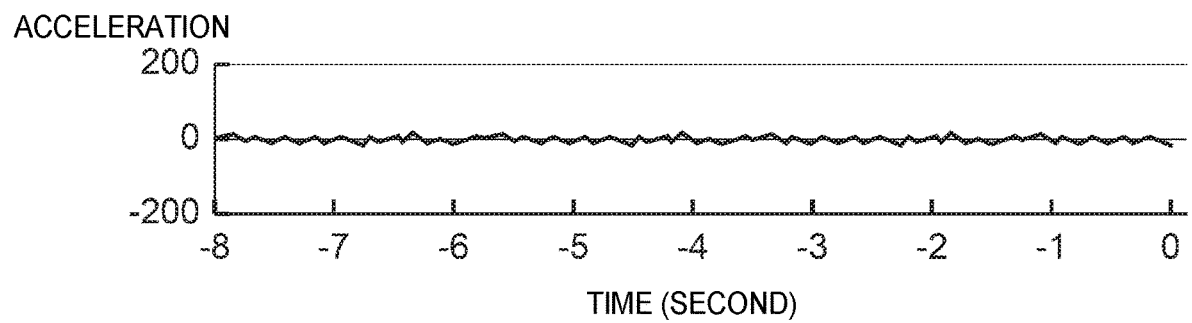
FIG. 25 is a diagram for explaining the periodic component determination process.

FIG. 25 through FIG. 28 are diagrams corresponding to the analytical data forming process in the step S41. FIG. 25 shows the state in which the user 4 takes a rest, and is therefore not doing the periodic exercise. On this occasion, the acceleration takes a small value. The analytical data forming section 26 obtains the data corresponding to 1 second from the body motion sensor 10. Then, the analytical data forming section 26 combines the body motion signal in the period from 1 second ago to the present with the body motion signal in the period from 8 seconds ago to 1 second ago to obtain the body motion signal in the period from 8 seconds ago to the present. Therefore, the body motion signal corresponding to 8 seconds is used as the short-term analytical data. It should be noted that the sampling frequency as the frequency at which the body motion sensor 10 obtains the data is not particularly limited providing the periodic exercise can be detected, and is preferably in a range of 20 Hz through 100 Hz. Further, the sampling frequency is preferably in a range of 30 Hz through 40 Hz. On this occasion, it is possible to set the number of data to a computable number, and at the same time, set the number of data to a number with which the periodic exercise can be detected.

Figure 26:
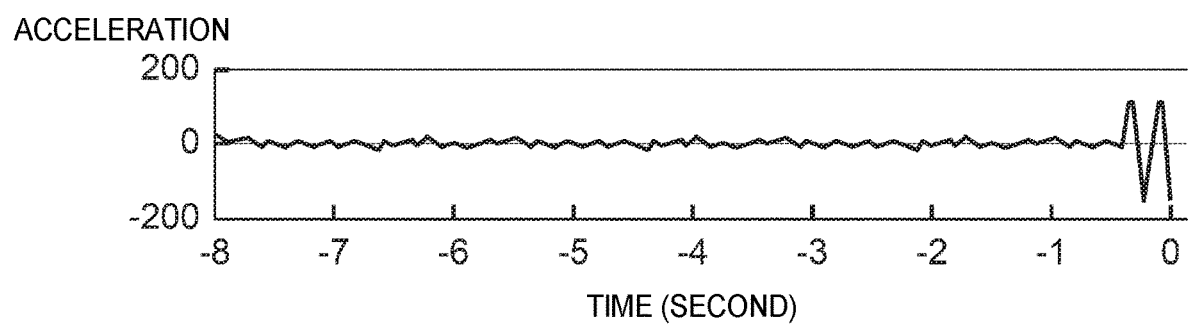
FIG. 26 is a diagram for explaining the periodic component determination process.

FIG. 26 shows the state in which the user 4 has started the periodic exercise. Therefore, in the short-term analytical data, the periodic component is absent in the period of −8 through −1 second, and is included in the period of −1 through 0 second.

Figure 27:
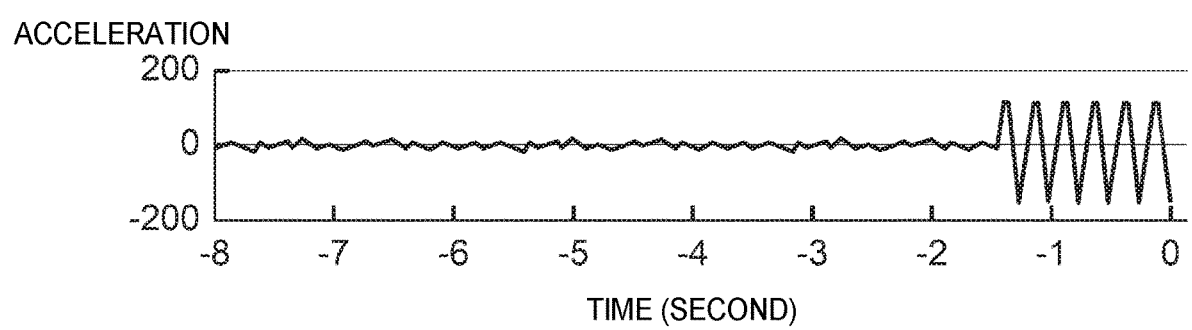
FIG. 27 is a diagram for explaining the periodic component determination process.

FIG. 27 shows the state in which 1.5 second has elapsed after the user 4 has started the periodic exercise. In the short-term analytical data, the periodic component is absent in the period of −8 through −2 second, and is included in the period of −2 through 0 second.

Figure 28:
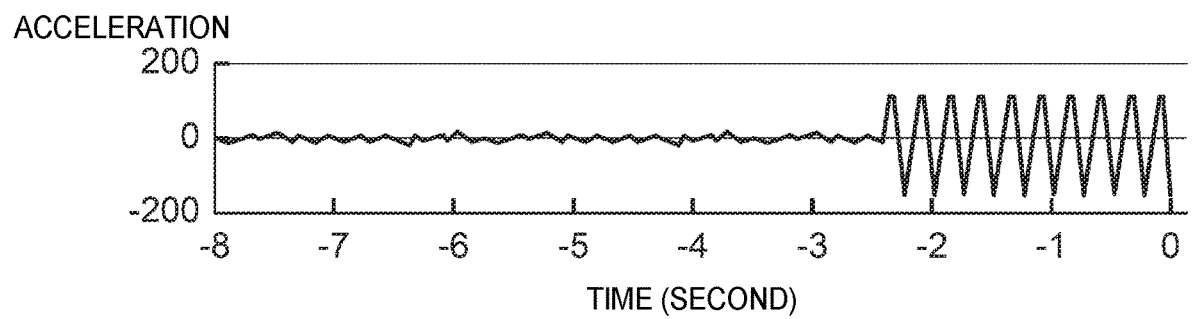
FIG. 28 is a diagram for explaining the periodic component determination process.

FIG. 28 shows the state in which 2.5 second has elapsed after the user 4 has started the periodic exercise. In the short-term analytical data, the periodic component is absent in the period of −8 through −3 second, and is included in the period of −3 through 0 second. As described above, since the short-term analytical data is formed of the data corresponding to 8 seconds, the amount of the periodic component included in the short-term analytical data is small immediately after the user 4 has started the periodic exercise. As the time elapses from the start of the repetitive motion, the amount of the periodic component included in the short-term analytical data increases.

In the analytical data forming section 26, in the case in which the periodic component is included in the period of −1 through 0 second, the time at which the data is obtained is stored to the memory 9. Further, in the case in which the periodic component is present in the period of −8 through −1 second in the short-term analytical data, and the periodic component is not included in the period of −1 through 0 second, the time at which the data is obtained is also stored to the memory 9. Therefore, it is arranged that in the case in which the determination has been made in the periodicity determination process in the step S47, the time at which presence or absence of the periodic component has been changed can be identified.

Figure 29:
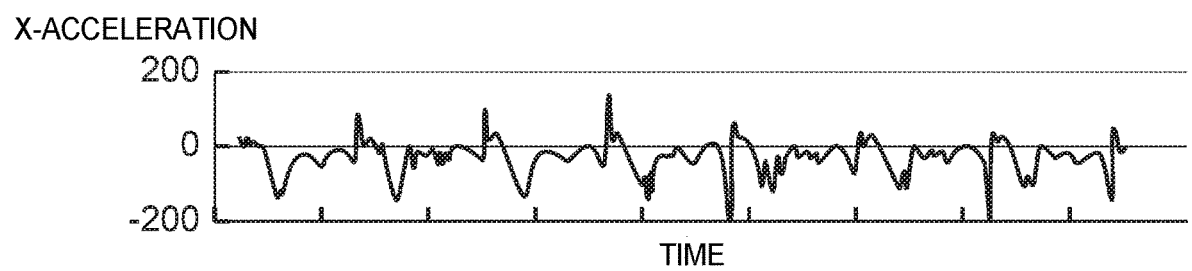
FIG. 29 is a diagram for explaining the periodic component determination process.
Figure 30:
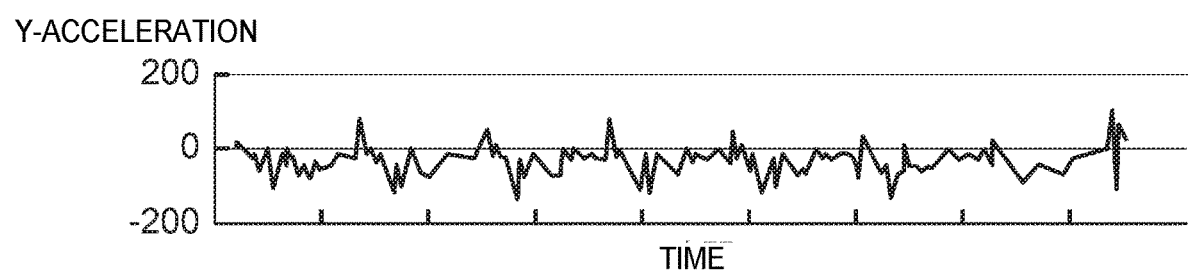
FIG. 30 is a diagram for explaining the periodic component determination process.
Figure 31:
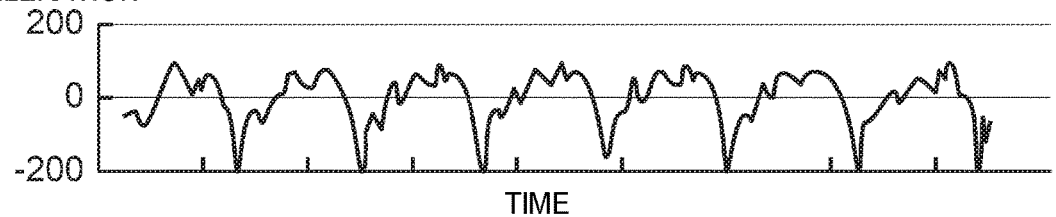
FIG. 31 is a diagram for explaining the periodic component determination process.
Figure 32:
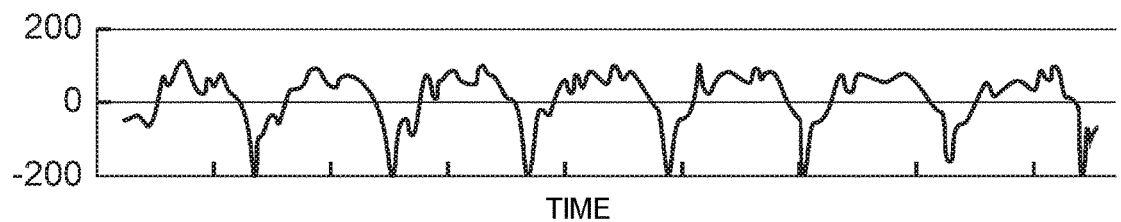
FIG. 32 is a diagram for explaining the periodic component determination process.

FIG. 29 through FIG. 35 are diagrams corresponding to the short-term periodicity determination process in the step S42. FIG. 29 shows the transition of the acceleration detected by the X-acceleration sensor 16. FIG. 30 shows the transition of the acceleration detected by the Y-acceleration sensor 17. FIG. 31 shows the transition of the acceleration detected by the Z-acceleration sensor 18.

Since the motion of the arm of the user 4 is a motion in the three-dimensional space, the waveforms respectively detected by the X-acceleration sensor 16, the Y-acceleration sensor 17, and the Z-acceleration sensor 18 are different from each other. The periodicity calculation section 27 calculates the acceleration waveform of a first principal component shown in FIG. 32 using a principal component analysis method on the outputs of the three acceleration sensors. The acceleration waveform of the first principal component is an acceleration waveform obtained by performing the coordinate rotation so as to increase the variance of the acceleration. The acceleration waveform of the first principal component is used as the short-term analytical data. The second principal component and the third principal component are not used.

Figure 33:
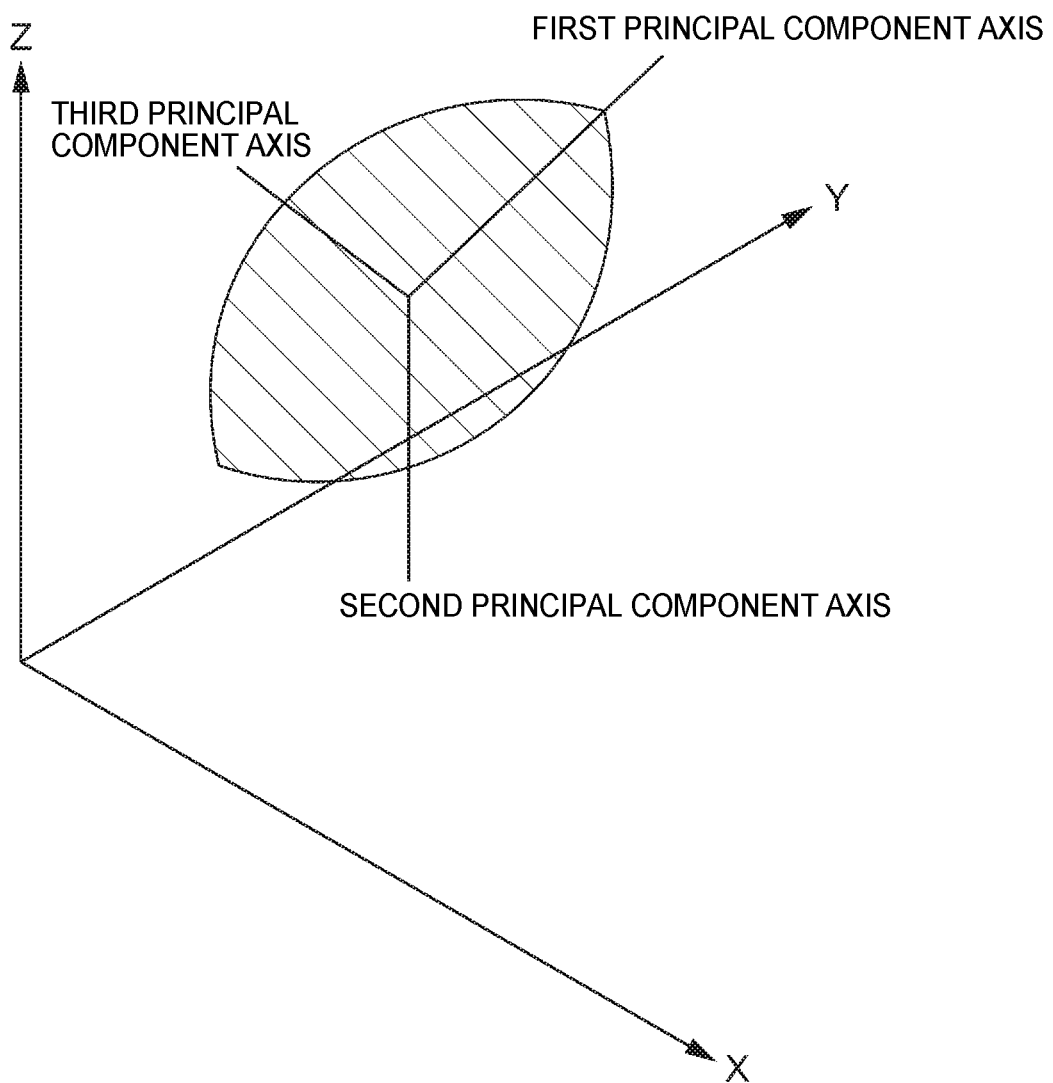
FIG. 33 is a diagram for explaining the periodic component determination process.

FIG. 33 is a distribution chart of the acceleration data. Further, the distribution chart is a chart showing a concept of the distribution chart obtained by plotting the accelerations detected by the X-acceleration sensor 16, the Y-acceleration sensor 17, and the Z-acceleration sensor 18 at the same time as the coordinate data of (X, Y, Z), respectively. The distribution of the acceleration (X, Y, Z) forms an ellipsoidal body elongated in one direction. In this case, the direction of the long axis of the ellipsoidal body corresponds to a first principal component axis. Further, when drawing the perpendicular to the first principal component axis from the value of the acceleration (X, Y, Z), the value on the first principal component axis is defined as the first principal component of the acceleration (X, Y, Z). Then, by calculating the first principal component of the acceleration (X, Y, Z), the acceleration waveform of the first principal component shown in FIG. 32 can be obtained.

Figure 34:
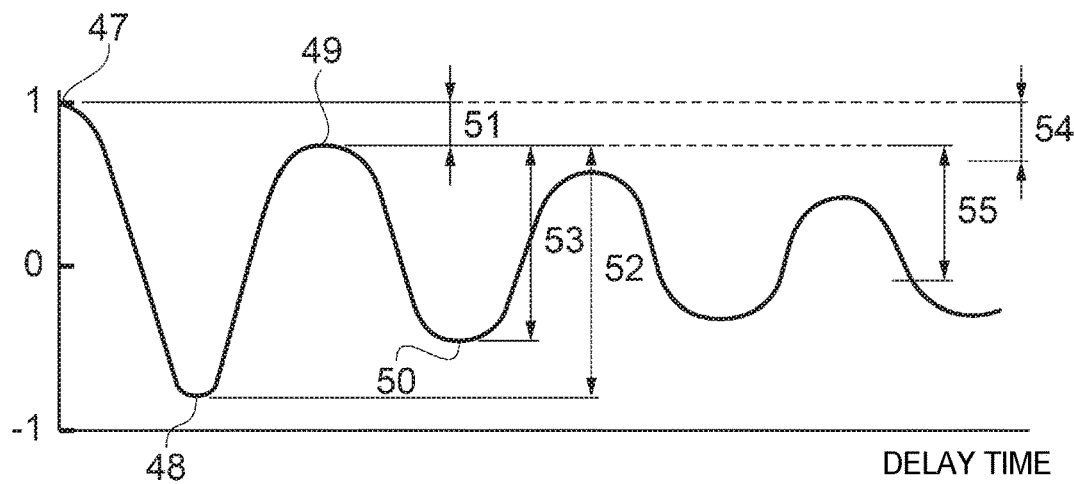
FIG. 34 is a diagram for explaining the periodic component determination process.
Figure 35:
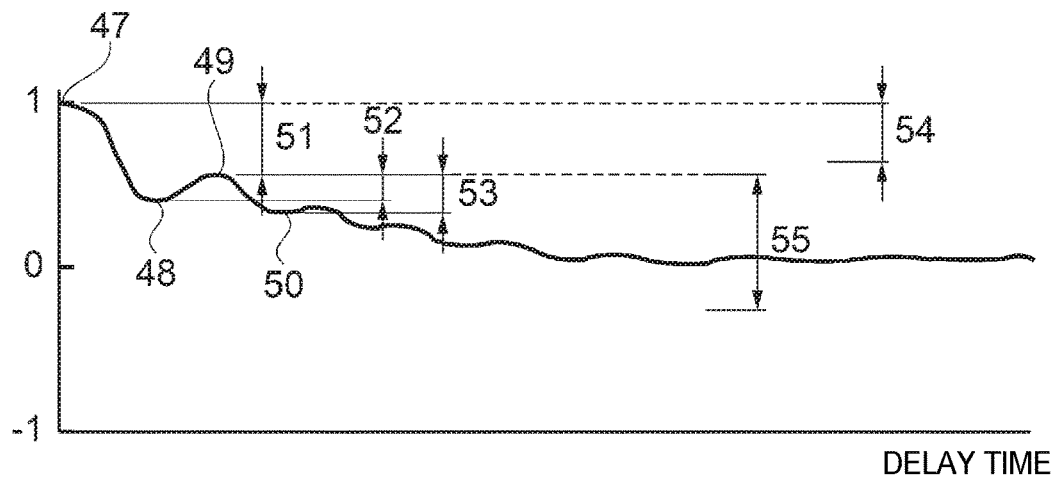
FIG. 35 is a diagram for explaining the periodic component determination process.

FIG. 34 and FIG. 35 show waveforms representing the auto-correlation function of the short-term analytical data. The waveform representing the auto-correlation function is referred to as an auto-correlation waveform. The auto-correlation function is known to the public, and the description thereof will be omitted. FIG. 34 shows the auto-correlation waveform in the case in which the amount of the periodic component is high, and FIG. 35 shows the auto-correlation waveform in the case in which the amount of the periodic component is low. In the waveforms, a part protruding upward in the drawing is defined as a convex, and a part protruding downward in the drawing is defined as a concave. A peak of the waveform forming the convex at the delay time of 0 is defined as a first peak 47. The most concave point of the concave located on the right of the first peak 47 in the drawing is defined as a first bottom 48. Further, the most convex point of the convex located on the right of the first bottom 48 in the drawing is defined as a second peak 49. Further, the most concave point of the concave located on the right of the second peak 49 in the drawing is defined as a second bottom 50.

A difference between the first peak 47 and the second peak 49 is defined as a peak difference 51. A difference between the first bottom 48 and the second peak 49 is defined as a first wave height 52. A difference between the second bottom 50 and the second peak 49 is defined as a second wave height 53. The memory 9 stores determination data 23 for determining the periodic component of the waveform. The determination data 23 includes a peak difference determination value 54 and a wave height determination value 55.

The periodicity calculation section 27 makes three determinations of first through third determinations to determine presence or absence of the periodic component in the short-term analytical data. In the first determination, the peak difference 51 and the peak difference determination value 54 are compared to each other. In the case in which the peak difference 51 is equal to or smaller than the peak difference determination value 54, the determination that "the periodic component is present" is made. In the second determination, the first wave height 52 and the wave height determination value 55 are compared to each other. In the case in which the first wave height 52 is equal to or larger than the wave height determination value 55, the determination that "the periodic component is present" is made. In the third determination, the second wave height 53 and the wave height determination value 55 are compared to each other. In the case in which the second wave height 53 is equal to or larger than the wave height determination value 55, the determination that "the periodic component is present" is made.

Then, in the case in which all of the first determination, the second determination, and the third determination result in the determination that "the periodic component is present," the determination that "the periodic component is present" in the short-term analytical data is made. In the case in which any one of the first determination, the second determination, and the third determination results in the determination that "the periodic component is absent," the determination that "the periodic component is absent" in the short-term analytical data is made.

In the auto-correlation waveform shown in FIG. 34, the peak difference 51 is equal to or smaller than the peak difference determination value 54, and the determination that "the periodic component is present" is made in the first determination. The first wave height 52 is equal to or larger than the wave height determination value 55, and therefore, the determination that "the periodic component is present" is made in the second determination. The second wave height 53 is equal to or larger than the wave height determination value 55, and therefore, the determination that "the periodic component is present" is made in the third determination. In all of the first determination, the second determination, and the third determination, the determination that "the periodic component is present" is made. Therefore, the determination that "the periodic component is present" in the short-term analytical data is made.

In the auto-correlation waveform shown in FIG. 35, the peak difference 51 is larger than the peak difference determination value 54, and the determination that "the periodic component is absent" is made in the first determination. The first wave height 52 is smaller than the wave height determination value 55, and therefore, the determination that "the periodic component is absent" is made in the second determination. The second wave height 53 is smaller than the wave height determination value 55, and therefore, the determination that "the periodic component is absent" is made in the third determination. The determination that "the periodic component is absent" is made in the second determination and the third determination. Therefore, the determination that "the periodic component is absent" in the short-term analytical data is made.

As described above, by making the determination on presence or absence of the periodic component using the peak difference 51, the first wave height 52, and the second wave height 53, it is possible to make the determination in a shorter period of time compared to the case of performing the Fourier transformation. After the step S42, the step S43 through the step S47 are executed to terminate the periodic component determination process.

As described above, according to the present embodiment, the following advantages are obtained.

(1) According to the present embodiment, the portable electronic apparatus 1 is provided with the operation section 12, the body motion sensor 10, the timing section 11, and the processing section 7. The operation section 12 receives the operation of the user 4 instructing the rest start, and then outputs the rest start signal. The body motion sensor 10 outputs the body motion signal based on the motion of the user 4. The timing section 11 measures the rest time for which the user 4 takes a rest. Further, the processing section 7 is electrically connected to the operation section 12, the body motion sensor 10, and the timing section 11.

In the case in which the user 4 makes the operation of instructing to start the rest, the operation section 12 outputs the rest start signal to the processing section 7. Then, the processing section 7 makes the timing section 11 start the measurement of the rest time. In the case in which the user 4 makes the repetitive motion, the processing section 7 detects the periodic component based on the motion of the user 4 in the body motion signal. In the case in which the user 4 stops the repetitive motion, the periodic component based on the motion of the user 4 is not detected by the processing section 7 in the body motion signal. Then, in the case in which the user 4 takes a rest, the repetitive motion is not performed for a predetermined period. When the processing section 7 fails to detect the periodic component based on the motion of the user 4 in the body motion signal for the predetermined period, the processing section 7 makes the timing section 11 start the measurement of the rest time. Then, the timing section 11 starts the measurement of the rest time. Therefore, even in the case in which the user 4 forgets to operate the operation section 12 when taking a rest, it is possible for the portable electronic apparatus 1 to start the measurement of the rest time.

(2) According to the present embodiment, in the case in which the user 4 makes the operation of instructing the start of the exercise, the operation section 12 receives the operation of instructing the start of the exercise and then outputs the exercise start signal to the processing section 7. Subsequently, in the case in which the user 4 makes the operation of instructing the start of the rest, the operation section 12 receives the operation of instructing the start of the rest and then outputs the rest start signal to the processing section 7. On this occasion, the processing section 7 detects the exercise start signal, and then detects the rest start signal. Then, the processing section 7 makes the timing section 11 start the measurement of the rest time, and therefore, the measurement of the rest time by the timing section 11 is started. Therefore, it is possible to surely start the measurement of the rest time by the timing section 11 based on the instruction of the user 4.

In the case in which the user 4 makes the operation of instructing the start of the exercise, the operation section 12 receives the operation of instructing the start of the exercise and then outputs the exercise start signal to the processing section 7. Subsequently, in the case in which the user 4 does not make the repetitive motion, the periodic component based on the motion of the user 4 is not detected by the processing section 7 in the body motion signal. When the processing section 7 fails to detect the periodic component based on the motion of the user 4 in the body motion signal for the predetermined period, the processing section 7 makes the timing section 11 start the measurement of the rest time. Then, the timing section 11 starts the measurement of the rest time. Therefore, even in the case in which the user 4 makes the operation of instructing to start the exercise, but forgets to make the operation of instructing to start the rest, it is possible for the portable electronic apparatus 1 to start the measurement of the rest time.

(3) According to the present embodiment, the timing section 11 measures the exercise time for which the user 4 does the exercise in addition to the rest time. Then, in the case in which the user 4 makes the repetitive motion, the timing section 11 measures the exercise time for which the user 4 does the exercise. In the case in which the user 4 stops the repetitive motion, the processing section 7 turns to the state of not detecting the periodic component. In the case in which the user 4 resumes the repetitive motion within a predetermined period, the processing section 7 detects the periodic component within the predetermined period after the processing section 7 has turned to the state of not detecting the periodic component. On this occasion, the processing section 7 makes the timing section 11 continue the measurement of the exercise time. Therefore, in the case in which the user 4 resumes the repetitive motion after once stopping the repetitive motion within the predetermined period, the timing section 11 continuously measures the exercise time. As a result, even in the case in which the repetitive motion is stopped within the predetermined period while the user 4 is doing the exercise, it is possible for the user 4 to make the portable electronic apparatus 1 continue the measurement of the exercise time.

(4) According to the present embodiment, the portable electronic apparatus 1 is provided with the display panel 6. The display panel 6 displays the information from the timing section 11. Then, when the timing section 11 measures the rest time, the display panel 6 displays the rest information related to the rest time. Therefore, it is possible for the user 4 to look at the display panel 6 to check the information such as the time having elapsed from the start of the rest.

(5) According to the present embodiment, after starting the measurement of the rest time, the measurement of the rest time continues. On this occasion, when the periodic component based on the motion of the user 4 is detected in the body motion signal for the predetermined period, the measurement of the rest time by the timing section 11 is terminated. Therefore, even in the case in which the user 4 forgets to operate the operation section 12, it is possible to terminate the measurement of the rest time.

(6) According to the present embodiment, the portable electronic apparatus 1 is provided with the operation section 12, the body motion sensor 10, the timing section 11, the display panel 6, and the processing section 7. The operation section 12 receives the operation of the user 4 instructing the rest start, and then outputs the rest start signal. The body motion sensor 10 outputs the body motion signal based on the motion of the user 4. The timing section 11 measures the rest time for which the user 4 takes a rest. The display panel 6 displays the information from the timing section 11. Further, the processing section 7 is electrically connected to the operation section 12, the body motion sensor 10, the timing section 11, and the display panel 6.

In the case in which the user 4 makes the operation of instructing to start the rest, the operation section 12 outputs the rest start signal to the processing section 7. Then, the processing section 7 makes the timing section 11 start the measurement of the rest time. In the case in which the user 4 makes the repetitive motion, the processing section 7 detects the periodic component based on the motion of the user 4 in the body motion signal. When the processing section 7 detects the body motion signal satisfying a predetermined condition, the fact that the user 4 is doing the repetitive motion is detected.

In the case in which the user 4 stops the repetitive motion, the periodic component based on the motion of the user 4 is not detected by the processing section 7 in the body motion signal. Then, in the case in which the user 4 takes a rest, the repetitive motion is not performed for a predetermined period. When the processing section 7 fails to detect the body motion signal satisfying the predetermined condition based on the motion of the user 4 in the body motion signal for the predetermined period, the processing section 7 makes the timing section 11 start the measurement of the rest time. Then, the timing section 11 starts the measurement of the rest time. Therefore, even in the case in which the user 4 forgets to make the rest instruction operation, it is possible for the portable electronic apparatus 1 to start the measurement of the rest time. Further, it is possible for the user 4 to look at the display panel 6 to check the rest information such as the time having elapsed from the start of the rest.

(7) According to the present embodiment, the body motion signal satisfying the predetermined condition is a signal including the continuous periodic component. Therefore, in the case in which the user 4 continuously performs the repetitive motions, it is possible for the processing section 7 to detect the fact that the user 4 is doing exercise.

(8) According to the present embodiment, the portable electronic apparatus 1 is provided with the operation section 12, the body motion sensor 10, the timing section 11, and the processing section 7. The operation section 12 receives the operation of the user 4 instructing the termination of the rest, and then outputs the rest termination signal. The body motion sensor 10 outputs the body motion signal based on the motion of the user 4. The timing section 11 measures the rest time for which the user 4 takes a breath. Further, the processing section 7 is electrically connected to the operation section 12, the body motion sensor 10, and the timing section 11.

In the case in which the user 4 makes the rest termination instruction operation, the operation section 12 outputs the rest termination signal to the processing section 7. Then, the processing section 7 makes the timing section 11 terminate the measurement of the rest time. In the case in which the user 4 forgets to make the rest termination instruction operation, the operation section 12 does not output the rest termination signal to the processing section 7. Then, the processing section 7 makes the timing section 11 continue the measurement of the rest time. Even on this occasion, in the case in which the user 4 makes the repetitive motion, the processing section 7 detects the periodic component based on the motion of the user 4 in the body motion signal. When the processing section 7 detects the periodic component based on the motion of the user 4 in the body motion signal, the processing section 7 makes the timing section 11 terminate the measurement of the rest time. Then, the timing section 11 terminates the measurement of the rest time. Therefore, even in the case in which the user 4 forgets to make the operation of instructing the termination of the rest, it is possible for the portable electronic apparatus 1 to terminate the measurement of the rest time.

(9) According to the present embodiment, the portable electronic apparatus 1 measures the exercise time in addition to the rest time. The operation section 12 receives the operation of the user 4 instructing the termination of the exercise, and then outputs the exercise termination signal. In the case in which the processing section 7 detects the exercise termination signal while the timing section 11 is measuring the exercise time, and the processing section 7 fails to detect the periodic component, the timing section 11 terminates the measurement of the exercise time. In other words, in the case in which the user 4 stops the repetitive motion and makes the exercise termination instruction operation, the timing section 11 terminates the measurement of the exercise time.

In the case in which the processing section 7 detects the exercise termination signal while the timing section 11 is measuring the exercise time, and the processing section 7 detects the periodic component, the timing section 11 continues the measurement of the exercise time. In other words, in the case in which the user 4 continues the repetitive motion, and makes the exercise termination instruction operation, the timing section 11 continues the measurement of the exercise time. Therefore, in the case in which the operation of instructing the exercise termination is an erroneous operation, it is possible for the timing section 11 to continue the measurement of the exercise time.

(10) According to the present embodiment, the portable electronic apparatus 1 is provided with the memory 9, and the memory 9 stores the time at which the operation section 12 outputs the rest termination signal. In the case in which the user 4 makes the edit instruction operation of the exercise time, the operation section 12 receives the edit instruction operation of the user 4. Then, the operation section 12 outputs the edit signal to the processing section 7. The processing section 7 detects the edit signal to terminate the rest time at the time at which the rest termination signal is output. Therefore, it is possible to correct the rest time into the correct time in the case in which the rest termination signal is not caused by an erroneous operation.

(11) According to the present embodiment, the portable electronic apparatus 1 is provided with the display panel 6. The display panel 6 displays the information from the timing section 11. Then, when the timing section 11 measures the rest time, the display panel 6 displays the information representing the rest time. Therefore, it is possible for the user 4 to look at the display panel 6 to check the time having elapsed from the start of the rest.

It should be noted that the present embodiment is not limited to the embodiment described above, but a variety of modifications or improvements can also be added by those skilled in the art within the technical concept of the invention. Some modified examples will be described below.

Modified Example 1

In the embodiment described above, the acceleration sensors are used as the body motion sensor 10. Besides the acceleration sensors, a gyro sensor can be used. In the case of installing the gyro sensor in the portable electronic apparatus 1, when the user 4 makes the periodic motion, the gyro sensor outputs the signal including the periodic component. Therefore, it is possible to use the gyro sensor as the body motion sensor 10.

Modified Example 2

In the embodiment described above, the second-scale measurement value is displayed on the display panel 6. It is also possible to display a $1/100$ second-scale measurement value on the display panel 6. Thus, the user 4 can more finely analyze the time.

Modified Example 3

In the embodiment described above, whether or not the periodic component is included in the waveform is determined in the short-term periodicity determination process in the step S42. On this occasion, the peak difference 51 is compared with the peak difference determination value 54. Further, the first wave height 52 and the second wave height 53 are compared with the wave height determination value 55. The method of determining whether or not the periodic component is included in the waveform is not limited thereto. It is also possible to use discrete Fourier transform method. It is also possible to use a variety of methods of determining the periodic component besides the above.

Modified Example 4

As shown in the embodiment described above, it is possible to use a single push button 5, or it is also possible to use a plurality of push buttons 5. In the case in which the single push button 5 is used, it is also possible to adopt a configuration in which different signals are output by the operation of the single button in accordance with the situation (during the exercise, during the rest) of the user 4 as described below.

In the first case in which the button is pressed during the exercise, the rest start signal is output from the operation section 12 to the processing section 7. Then, in the case in which the processing section 7 fails to detect the periodic component based on the motion of the user 4 in the body motion signal, the timing section 11 starts the measurement of the rest time.

In the second case in which the same button as in the first case is pressed during the rest, the rest termination signal is output from the operation section 12 to the processing section 7. Then, in the case in which the processing section 7 detects the periodic component based on the motion of the user 4 in the body motion signal, the timing section 11 terminates the measurement of the rest time. By adopting this process, even with the signal pushbutton 5, switching between the start and the termination of the measurement of the rest time can be achieved.

Modified Example 5

In the embodiment described above, in both of the first periodic component determination process in the step S3 and the second periodic component determination process in the step S5, whether or not the processing section 7 detects the periodic component based on the motion of the user 4 in the body motion signal in FIG. 3. Therefore, it is also possible to integrate the step S3 and the step S5 into a single step. Further, it is also possible to make the process branch in accordance with the state.

Similarly, in both of the fifth periodic component determination process in the step S26 and the sixth periodic component determination process in the step S27, whether or not the processing section 7 detects the periodic component based on the motion of the user 4 in the body motion signal in FIG. 17. Therefore, it is also possible to integrate the step S26 and the step S27 into a single step. Further, it is also possible to make the process branch in accordance with the state.

What is claimed is:

1. A portable electronic apparatus for use with a user, the portable electronic apparatus comprising:
    at least one input configured to: (a) receive an operation of the user initiating a start of a rest state of the user, and (b) output a rest start signal representing the start of the rest state of the user based on the operation of the user;
    a body motion sensor configured to: (i) measure a motion of the user, (ii) and output a body motion signal based on the measured motion of the user; and
    a processor programmed to:
        detect whether the rest start signal is being outputted,
        detect whether a periodic component is present within a predetermined period based on the body motion signal, and
        start measurement of a rest time of the user in response to both of: (1) the rest start signal not being outputted, and (2) the periodic component not being present within the predetermined period.

2. The portable electronic apparatus according to claim 1, wherein
    the at least one input receives the operation of the user to output an exercise start signal representing a start of an exercise, and
    the processor starts measurement of the rest time in response to at least one of: (A) the processor detecting the rest start signal after detecting the exercise start signal, and (B) the processor not detecting the rest start signal and the periodic component not being present.

3. The portable electronic apparatus according to claim 1, wherein
    the processor measures an exercise time for which the user performs an exercise based on the body motion signal, and
    the processor continues the measurement of the exercise time in response to the processor detecting the periodic component within a predetermined period after not detecting the periodic component while the processor measures the exercise time.

4. The portable electronic apparatus according to claim 2, wherein
    the processor measures an exercise time for which the user performs an exercise based on the body motion signal, and
    the processor continues the measurement of the exercise time in response to the processor detecting the periodic component within a predetermined period after not detecting the periodic component while the processor measures the exercise time.

5. The portable electronic apparatus according to claim 1, further comprising:
    an image display configured to display rest information related to the rest time measured by the processor.

6. The portable electronic apparatus according to claim 2, further comprising:
    an image display configured to display rest information related to the rest time measured by the processor.

7. The portable electronic apparatus according to claim 6, wherein
    the rest information includes an amount of remaining time for a predetermined interval of rest time.

8. The portable electronic apparatus according to claim 6, wherein
    the rest information includes an amount of time until the user starts subsequent exercise.

9. The portable electronic apparatus according to claim 1, wherein
    the processor terminates the measurement of the rest time in response to the processor detecting the periodic component is present after starting the measurement of the rest time.

10. A portable electronic apparatus for use with a user, the portable electronic apparatus comprising:
    at least one input configured to: (a) receive an operation of the user initiating a start of a rest state of the user, and (b) output a rest start signal representing the start of the rest state of the user based on the operation of the user;
    a body motion sensor configured to: (i) measure a motion of the user, and (ii) output a body motion signal based on the measured motion of the user;
    an image display adapted to display information; and
    a processor programmed to:
        determine whether the rest start signal is being outputted,
        determine whether a predetermined condition is satisfied within a predetermined period based on the body motion signal for the predetermined period, and
        start measurement of a rest time of the user and display rest information related to the measured rest time in the image display in response to both of: (1) determining that the rest start signal being not being outputted, and (2) the predetermined condition being not satisfied within the predetermined period.

11. The portable electronic apparatus according to claim 10, wherein
    the processor determines that the predetermined condition is satisfied when a periodic component is continuously present within the predetermined period.

12. A portable electronic apparatus for use with a user, the portable electronic apparatus comprising:
    at least one input configured to: (a) receive an operation of the user initiating a termination of a rest state of the user, and (b) output a rest termination signal representing the termination of the rest state of the user based on the operation of the user;
    a body motion sensor configured to: (i) measure a motion of the user, and (ii) output a body motion signal based on the measured motion of the user; and
    a processor programmed to:
        determine whether the rest termination signal is being outputted,
        determine whether the body motion signal includes a periodic component, and terminate measurement of a rest time of the user in response to both of: (1) the rest termination signal not being outputted, and (2) the body motion signal including the periodic component.

13. The portable electronic apparatus according to claim 12, wherein the processor measures exercise time for which the user performs an exercise, the at least one input receives an operation of the user to output an exercise termination signal representing a termination of the exercise, the processor terminates the measurement of the exercise time in response to: (A) the processor detecting the exercise termination signal while the processor is measuring the exercise time, and (B) the processor not detecting the presence of the periodic component, and the processor continues the measurement of the exercise time in response to: (1) the processor detecting the exercise termination signal while the processor is measuring the exercise time, and (2) the processor detecting the presence of the periodic component.

14. The portable electronic apparatus according to claim 13, further comprising:

a memory that stores a time at which the processor outputs the rest termination signal, wherein the at least one input is configured to receive the operation of the user instructing an edit, and to output an edit signal based on the operation of the user instructing the edit, and when the processor detects the edit signal, the processor terminates the rest time at a time at which the rest termination signal is output.

15. The portable electronic apparatus according to claim 12, further comprising:

an image display configured to display the rest time when the rest time is being measured.

16. The portable electronic apparatus according to claim 13, further comprising:

an image display configured to display the rest time when the rest time is being measured.

17. The portable electronic apparatus according to claim 14, further comprising:

an image display configured to display the rest time when the rest time is being measured.

* * * * *